United States Patent [19]
Caras et al.

[11] Patent Number: 5,264,357
[45] Date of Patent: Nov. 23, 1993

[54] NUCLEIC ACIDS VECTORS AND CELLS FOR THE SYNTHESIS OF MEMBRANE ANCHOR FUSION POLYPEPTIDES

[75] Inventors: Ingrid W. Caras, San Francisco, Calif.; Michael A. Davitz, Riverdale; Victor Nussenzweig, New York, both of N.Y.; David W. Martin, Jr., San Francisco, Calif.

[73] Assignee: Genentech, Inc., South San Francisco, Calif.

[21] Appl. No.: 811,048

[22] Filed: Dec. 19, 1991

Related U.S. Application Data

[60] Division of Ser. No. 83,757, Aug. 6, 1987, Pat. No. 5,109,113, which is a continuation-in-part of Ser. No. 859,107, May 2, 1986, abandoned, and a continuation-in-part of Ser. No. 738,171, May 24, 1985, abandoned, and a continuation-in-part of PCT/US86/01/77, May 23, 1986, abandoned.

[51] Int. Cl.[5] .................... C12N 15/12; C12N 5/10
[52] U.S. Cl. ........................... 435/240.1; 435/240.2; 435/252.3; 435/69.7; 435/320.1; 536/23.4
[58] Field of Search ................... 536/27, 23.4; 435/320.1, 240.1, 240.2, 252.3, 69.7

[56] References Cited

U.S. PATENT DOCUMENTS 4,480,041 10/1984 Myles et al. ........................ 436/508

FOREIGN PATENT DOCUMENTS 8607062 12/1986 PCT Int'l Appl. .

OTHER PUBLICATIONS

Medof et al., PNAS 84:2007-2011 (1987).
Caras et al., Science 288:1280-1282 (1987).
Holers et al., Immunology Today 6(6): 188-192 (1985).
Ferguson et al., J. Biol. Chem. 260(27):14547-55 (1985).
Medof et al., Biochemistry 25:6740-6747 (1986).
Caras et al., Nature 325:545-548 (1987).
Templeton et al. "Construction & Expression of a Recombinant DNA Gene . . . " Molecular & Cellular Biology 4(2):282-289, Feb. 1984.
Iida, K. & Nussenzweig, V., J. Exp. Med. 153:1138-1150 (1981).
Medof et al., J. Exp. Med. 156:1739-1754 (1982).
Pangburn et al., J. Exp. Med. 157:1971-1980 (1983).
Medof & Nussenzweig, J. Exp. Med. 159:1669-1685 (1984).
Medof et al., J. Exp. Med. 160:1558-1578 (1984).
Nicholson-Weller et al., J. Immunol. 129(1):184-189 (1982).
Fearon, D. T., P.N.A.S. 76(11):5867-5871 (1979).
Ross et al., J. Immunol. 129(5):2051-2060 (1982).
Medicus et al., Eur. J. Immunol. 13:465-470 (1983).

*Primary Examiner*—Nina Ossanna
*Attorney, Agent, or Firm*—Renee A. Fitts

[57] ABSTRACT

Novel fusions of a phospholipid anchor domain and a polypeptide heterologous to the anchor domain donor polypeptide are provided for industrial use. Therapeutic administration of the fusions enables the targeting of biological activity to cell membrane surfaces.

4 Claims, 14 Drawing Sheets

Fig.1a.

```
                                                         fnu4HI
                                             mspI         hgaI
                                             scrFI        thaI
                             fnu4HI           nciI        hinPI
                             bbvI             hinfI hpaII hhaI                       hinPI
              aluI  hinfI                                                             hhaI
1 CCGCTGGGCG TAGCTGCGAC TCGGCGGAGT CCCGGCGGCG CGTCCTTGTT                    fnu4HI
  GGCGACCCGC ATCGACGCTG AGCCGCCTCA GGGCCGCCGC GCAGGAACAA              thaI   fnu4HI
                                                                      sacII  bbvI
          hinPI              xmaIII                                   bsp1286 haeII
          hhaI               fnu4HI                     CCGAGCGTGC CCGGCGGCT
          bssHII             thaI                       GGCTCGCACG GGCCGCCGA
   mspI                      hinPI                      ProSerValP roAlaAlaLeu
   hpaII hinPI               hhaI                              -30
   scrFI hhaI       thaI haeIII
   nciI thaI nlaIII                                                  fnu4HI
  CTAACCCGGC GCGGCATGAC CGTCGGCGCG                                    bbvI
  GATTGGGCCG CGCCGTACTG GCAGCCGCGC                    mspI   fnu4HI
              MetTh      rValAlaArg        aluI fnu4HI hpaII bbvI
                                                bbvI   scrFI fnu4HI
              avaI                              aluI   nciI  bbvI
              mnlI                GGGAGCTGC CCCGGCTGCT GCTGCTGGTG CTGTTGTGCC
        mnlI               GGGGAGG CCCTCGACG GGGCCGACGA CGACGACCAC GACAACACGG
  101 GCCCCTCCTC           GlyGluLeuP roArgLeuLe uLeuLeuVal LeuLeuCysLeu
      CGGGAGGAG
      ProLeuLeu                                                     -10
          -20
       haeIII                haeIII
       xmaIII                haeI
       mspI                  hphI               rsaI
       hpaII                                    
       naeI
  TGCCGGCCGT GTGGGTGAC TGTGGCCTTC CCCCAGATGT ACCTAATGCC
  ACGGCCGGCA CACCCACTG ACACCGGAAG GGGGTCTACA TGGATTACGG
  ProAlaVa lTrpGlyAsp CysGlyLeuP roProAspva lProAsnAla
                       1                              10
```

Fig.1b.

```
              aluI             rsaI                  mnlI
                  haeIII           rsaIII                avaI                               ddeI
                                                                                              hinfI
201 CAGCCAGCTT TGGAAGGCCG TACAAGTTTT CCCGAGGATA CTGTAATAAC
    GTCGGTCGAA ACCTTCCGGC ATGTTCAAAA GGGCTCCTAT GACATTATTG
    GlnProAlaL euGluGlyAr gThrSerPhe ProGluAspT hrValIleThr
                   20
            hindIII                               scrFI
        mboII alulI                                bstNI
    rsaI                                                       
    GTACAAATGT GAAGAAAGCT TTGTGAAAAT TCCTGGCGAG AAGGACTCAG
    CATGTTTACA CTTCTTTCGA AACACTTTTA AGGACCGCTC TTCCTGAGTC
    TyrLysCys GluGluSerP heValLysIl eProGlyGlu LysAspSerVal
       30
    sau3AI
    dpnI  bglI                                      mboII
301 TGATCTGCCT TAAGGGCAGT CAATGGTCAG ATATTGAAGA GTTCTGCAAT
    ACTAGACGGA ATTCCCGTCA GTTACCAGTC TATAACTTCT CAAGACGTTA
    IleCysLe  uLysGlySer GlnTrpSerA spIleGluGl uPheCysAsn
                  50                                  60
          fnu4HI nlaIV
       bbvI    banI                                       mnlI
    aluI mnlI bglI                            fokI
                                              sfaNI
    CGTAGCTGCG AGGTGCCAAC AAGGCTAAAT TCTGCATCCC TCAAACAGCC
    GCATCGACGC TCCACGGTTG TTCCGATTTA AGACGTAGGG AGTTTGTCGG
    ArgSerCysG luValProTh rArgLeuAsn SerAlaSerL euLysGlnPro
                                                    70
          ddeI                         rsaI
401 TTATATCACT CAGAATTATT TTCCAGTCGG TACTGTTGTG GAATATGAGT
    AATATAGTGA GTCTTAATAA AAGGTCAGCC ATGACAACAC CTTATACTCA
    TyrIleThr  GlnAsnTyrP heProValGl yThrValVal GluTyrGluCys
      80                                  90
     scrFI                               hphI
     bstNI                                      
       mboII
    GCCTCCAAGG TTACAGAAGA GAACCTTCTC TATCACCAAA ACTAACTTGC
    CGGAGGTTCC AATGTCTTCT CTTGGAAGAG ATAGTGGTTT TGATTGAACG
    ArgProGl yTyrArgArg GluProSerL euSerProLy sLeuThrCys
                  100                                  110
    draI  sau96I
       ahaIII  avaII              taqI                     nlaIII
501 CTTCAGAATT TAAAATGGTC CACAGCAGTC GAATTTGTA AAAAGAAATC
    GAAGTCTTAA ATTTTACCAG GTGTCGTCAG CTTAAACAT TTTTCTTTAG
    LeuGlnAsnL euLysTrpSe rThrAlaVal GluPheCysL ysLysLysSer
                  120
```

Fig.1c.

```
                 scrFI
                 ncil
                 mspI
                 hpaII                                              scrFI
                                                                    bstNI
                                                          rsaI
     ATGCCCTAAT  CCGGGAGAAA  TACGAAATGG  TCAGATTGAT  GTACCAGGTG
     TACGGGATTA  GGCCCTCTTT  ATGCTTTACC  AGTCTAACTA  CATGGTCCAC
     CysProAsn   ProGlyGluI  leArgAsnGl  yGlnIleAsp  ValProGlyGly
     130                                 140
                                         nlaIII                    rsaI
601  GCATATATT   TGGTGCAACC  ATCTCCTTCT  CATGTAACAC  AGGGTACAAA
     CGTATATAA   ACCACGTTGG  TAGAGGAAGA  GTACATTGTG  TCCCATGTTT
     IleLeuPh    eGlyAlaThr  IleSerPheS  erCysAsnTh  rGlyTyrLys
                 150                                               160
                                                     aluI
                                                     fnu4HI
                 taqI                                bbvI
     TTATTTGGCT  CGACTTCTAG  TTTTTGTCTT  ATTTCAGGCA  GCTCTGTCCA
     AATAAACCGA  GCTGAAGATC  AAAAACAGAA  TAAAGTCCGT  CGAGACAGGT
     LeuPheGlyS  erThrSerSe  rPheCysLeu  IleSerGlyS  erSerValGln
                                         170
     GTGGAGTGAC  CCGTTGCCAG  AGTGCAGAGA  AATTTATTGT  CCAGCACCAC
     CACCTCACTG  GGCAACGGTC  TCACGTCTCT  TTAAATAACA  GGTCGTGGTG
     TrpSerAsp   ProLeuProG  luCysArgGl  uIleTyrCys  ProAlaProPro
     180                                             190 nlaIII
                 nsiI
                 avaII                                             hphI           hgiAI
     CACAAATTGA  CAATGGAATA  ATTCAAGGGG  AACGTGACCA  TTATGGATAT
     GTGTTTAACT  GTTACCTTAT  TAAGTTCCCC  TTGCACTGGT  AATACCTATA
     GlnIleAs    pAsnGlyIle  IleGlnGlyG  luArgAspHi  sTyrGlyTyr
                 200                                               210 hphI      nlaIII   hgiAI
                                                                   hinfI              bsp1286
     AGACAGTCTG  TAACGTATGC  ATGTAATAAA  GGATTCACCA  TGATTGGAGA
     TCTGTCAGAC  ATTGCATACG  TACATTATTT  CCTAAGTGGT  ACTAACCTCT
     ArgGlnSerV  alThrTyrAl  aCysAsnLys  GlyPheThrM  etIleGlyGlu
801                                      220 rsaI                                              sau96I
                                                                   haeIII
     GCACTCTATT  TATTGTACTG  TGAATAATGA  TGAAGGAGAG  TGGAGTGGCC
     CGTGAGATAA  ATAACATGAC  ACTTATTACT  ACTTCCTCTC  ACCTCACCGG
     HisSerIle   TyrCysThrV  alAsnAsnAs  pGluGlyGlu  TrpSerGlyPro
     230                                             240
```

Fig.1d.

```
                                                      sau96I
                                                      nlaIV
                          bsmI        mnlI            avaII
       CACCACCTGA ATGCAGAGGA AAATCTCTAA CTTCCAAGGT CCCACCAACA
       GTGGTGGACT TACGTCTCCT TTTAGAGATT GAAGGTTCCA GGGTGGTTGT
  901  ProProGl uCysArgGly LysSerLeuT hrSerLysVa lProProThr
                     250                                  260
                                                              hphI
       GTTCAGAAAC CTACCACAGT AAATGTTCCA ACTACAGAAG TCTCACCAAC
       CAAGTCTTTG GATGGTGTCA TTTACAAGGT TGATGTCTTC AGAGTGGTTG
       ValGlnLysP roThrThrVa lAsnValPro ThrThrGluV alSerProThr
                                   270
             ddeI
       TTCTCAGAAA ACCACCACAA AAACCACCAC ACCAAATGCT CAAGCAACAC
       AAGAGTCTTT TGGTGGTGTT TTTGGTGGTG TGGTTTACGA GTTCGTTGTG
 1001  SerGlnLys ThrThrThrL ysThrThrTh rProAsnAla GlnAlaThrArg
                 280                                        290
                     scrFI                       nlaIII
             rsaI    bstNI
       GGAGTACACC TGTTCCAGG ACAACCAAGC ATTTTCATGA AACAACCCCA
       CCTCATGTGG ACAAGGTCC TGTTGGTTCG TAAAAGTACT TTGTTGGGGT
       SerThrPr oValSerArg ThrThrLysH isPheHisGl uThrThrPro
                     xmnI                                  310
                     nlaIV                           mRNA Splice Site
                                            mboII       bsp1286
       AATAAAGGAA GTGGAACCAC TTCAGGTACT ACCCGTCTTC TATCTGGCA
       TTATTTCCTT CACCTTGGTG AAGTCCATGA TGGGCAGAAG ATAGACCGT
 1101  AsnLysGlyS erGlyThrTh rSerGlyThr ThrArgLeuL euSerGlyHis
                              320
                                                       nlaIII
              hincII                                   styI
                                          hgaI        ncoI
       CACGTGTTTC ACGTTGACAG GTTTGCTTGG GACGGCTAGTA ACCATGGGCT
       GTGCACAAAG TGCAACTGTC CAAACGAACC CTGCGATCAT TGGTACCCGA
       ThrCysPhe ThrLeuThrG lyLeuLeuGl yThrLeuVal ThrMetGlyLeu
          330                                    340
                                  mboII              accI
             ddeI     mboII
       TGCTGACTTA GCCAAAGAAG AGTTAAGAAG AAAATACACA CAAGTATACA
       ACGACTGAAT CGGTTTCTTC TCAATTCTTC TTTTATGTGT GTTCATATGT
 1201  LeuThrAM
              *

GACTGTTCCT AGTTTCTTAG ACTTATCTGC ATATTGGATA AAATAAATGC
       CTGACAAGGA TCAAAGAATC TGAATAGACG TATAACCTAT TTTATTTACG
```

Fig.1e.

```
             mboII            sfaNI
      hgiAI              fokI
      bsp1286
1301  AATGTGCTC TTCATTTAGG ATGCTTTCAT TGTCTTTAAG ATGTGTTAGG
      TTAACACGAG AAGTAAATCC TACGAAAGTA ACAGAAATTC TACACAATCC hinfI
                             scrFI
                             bstNI              ddeI
      hincII
1401  AATGTCAACA GAGCAAGGAG AAAAAAGGCA GTCCTGGAAT CACATTCTTA
      TTACAGTTGT CTCGTTCCTC TTTTTTCCGT CAGGACCTTA GTGTAAGAAT mnlI                                        hinfI
1401  GCACACCTAC ACCTCTTGAA AATAGAACAA CTTGCAGAAT TGAGAGTGAT
      CGTGTGGATG TGGAGAACTT TTATCTTGTT GAACGTCTTA ACTCTCACTA 1501  TCCTTTCCTA AAAGTGTAAG AAAGCATAGA GATTTGTTCG TATTTAGAAT
      AGGAAAGGAT TTTCACATTC TTTCGTATCT CTAAACAAGC ATAAATCTTA sau3AI
                                                     dpnI
                                                     xhoII
      sau3AI    mnlI                                 bglII           ecoRV
1501  GGGATCACGA GGAAAAGAGA AGGAAAGTGA TTTTTTTCCA CAAGATCTGT ATTATTTGGA
      CCCTAGTGCT CCTTTTCTCT TCCTTTCACT AAAAAAAGGT GTTCTAGACA TAATAAACCT AATGTTATTT CCACTTATAA AGGAAATAAA AATGAAAAAC AAAATTGCTA
      TTACAATAAA GGTGAATATT TCCTTTATTT TTACTTTTTG TTTTAACGAT ddeI
                       mtmboII
1601  TATCAAAAGC AAATAAAAC CAATTCAGTC TCTTCTAAGC AAAATTGCTA
      ATAGTTTTCG TTTATTTTGG GTTAAGTCAG AGAAGATTCG TTTTAACGAT AAGAGAGATG AACCACATTA TAAAGTAATC TTTGGCTGTA AGGCATTTTC
      TTCTCTCTAC TTGGTGTAAT ATTTCATTAG AAACCGACAT TCCGTAAAAG draI                          nlaIII hphI
          sspI ahaIII
1701  ATCTTTCCTT CGGGTTGGCA AAATATTTA AAGGTAAACA TGCTGGTGAA
      TAGAAAGGAA GCCCAACCGT TTTATAAAT TTCCATTTGT ACGACCACTT
```

Fig.1f.

```
      scrFI
      bstNI                    hphI            mnlI                       mboII
                                                                   hinfI
      CCAGGGGTGT TGATGGTGAT AAGGGAGGAA TATAGAATGA AAGACTGAAT
      GGTCCCCACA ACTACCACTA TTCCCTCCTT ATATCTTACT TTCTGACTTA
                                                                   mboII
1801  CTTCCTTGTT GCACAAATAG AGTTTGGAAA AGCCCTGTGAA AGGTGTCTTC
      GAAGGAACAA CGTGTTTATC TCAAACCTTT TCGGACACTT TCCACAGAAG
                 draI
                 ahaIII                                  sspI
      TTTGACTTAA TGTCTTTAAA AGTATCCAGA GATACTACAA TAGTCAAATA
                                                         sspI
      AAACTGAATT ACAGAAATTT TCATAGGTCT CTATGATGTT ATCAGTTTAT
                              taqI
                              hinfI
1901  AGAAAGATT ATATATATATT TCTGAATCGA GATGTCCATA GTCAAATTTG
      TCTTTTCTAA TATATATAATAA AGACTTAGCT CTACAGGTAT CAGTTTAAAC
                         sspI
      TAAATCTTAT TCTTTTGTAA TATTTATTTA TATTTATTTA TGACAGTGAA
      ATTTAGAATA AGAAAACATT ATAAATAAAT ATAAATAAAT ACTGTCACTT
                                           mboII
                 nlaIII                    mboII                  mboII
2001  CATTCTGATT TTACATGTAA AACAAGAAAA GTTGAAGAAG ATATGTGAAG
      GTAAGACTAA AATGTACATT TTGTTCTTTT CAACTTCTTC TATACACTTC
                                sau3AI
                                dpnI
      AAAAATGTAT TTTTCCTAAA TAGAAATAAA TGATCCCATT TTTTGGTAAA
      TTTTTACATA AAAAGGATTT ATCTTTATTT ACTAGGGTAA AAAACCATTT
2101  AAAAAAAAAA AAAAA
      TTTTTTTTTT TTTTT
```

```
                    alu I              rsa I        mnl I
                         hae III            ava I
201 CAGCCAGCTT TGGAAGGCCG TACAAGTTTT CCCGAGGATA CTGTAATAAC
    GTCGGTCGAA ACCTTCCGGC ATGTTCAAAA GGGCTCCTAT GACATTATTG
    GlnProAlaL euGluGlyAr gThrSerPhe ProGluAspT hrValIleThr
                                20
    rsa I          hind III                   scrFI      ddeI
         mboII     aluI                       bstNI      hinfI
    GTACAAATGT GAAGAAAGCT TTGTGAAAAT TCCTGGCGAG AAGGACTCAG
    CATGTTTACA CTTCTTTCGA AACACTTTTA AGGACCGCTC TTCCTGAGTC
    TyrLysCys GluGluSerP heValLysIl eProGlyGlu LysAspSerVal
          30                                40
    sau3AI
    dpnI bglII                                    mboII
301 TGATCTGCCT TAAGGGCCAGT CAATGGTCAG ATATTGAAGA GTTCTGCAAT
    ACTAGACGGA ATTCCCGTCA GTTACCAGTC TATAACTTCT CAAGACGTTA
    IleCysLe uLysGlySer GlnTrpSerA spIleGluGl uPheCysAsn
                    50                                 60
    fnu4HI  nlaIV                              mnlI
    bbvI    banI                               fokI
    aluI  mnlII  bglII                         sfaNI
    CGTAGCTGCG AGGTGCCAAC TCCACGGTTG TCTGCATCCC TCAAACAGCC
    GCATCGACGC TCCACGGTTG AGGTGCCAAC AGACGTAGGG AGTTTGTCGG
    ArgSerCysG luValProTh rArgLeuAsn SerAlaSerL euLysGlnPro
                                 70
                                        rsaI
    ddeI       CAGAATTATT TTCCAGTCGG TACTGTGTG GAATATGAGT
401 TTATATCACT CAGAATTATT TTCCAGTCGG TACTGTGTG GAATATGAGT
    AATATAGTGA GTCTTAATAA AAGGTCAGCC ATGACAACAC CTTATACTCA
    TyrIleThr GlnAsnTyrP heProValGl yThrValVal GluTyrGluCys
         80                               90
    scrFI              mboII                  hphI
    bstNI
    GCCGTCCAGG TTACAGAAGA GAACCTTCTC TATCACCAAA ACTAACTTGC
    CGGCAGGTCC AATGTCTTCT CTTGGAAGAG ATAGTGGTTT TGATTGAACG
    ArgProGly TyrArgArg GluProSerL euSerProLy sLeuThrCys
                  100                              110
    draI   sau96I                      taqI              nlaIII
    ahaIII avaII
501 CTTCAGAATT TAAAATGGTC CACAGCAGTC GAATTTTGTA AAAAGAAATC
    GAAGTCTTAA ATTTTACCAG GTGTCGTCAG CTTAAAACAT TTTTCTTTAG
    LeuGlnAsnL euLysTrpSe rThrAlaVal GluPheCysL ysLysLysSer
                                120
```

Fig.2c.

```
                scrFI
                nciI
                mspI                                              scrFI
                hpaII                              rsaI           bstNI
    ATGCCCTAAT CCGGGAGAAA TACGAAATGG TCAGATTGAT AGTCTAACTA CATGGTCCAC
    TACGGGATTA GGCCCTCTTT ATGCTTTACC AGTCTAACTA TCAGATTGAT GTACCAGGTG
    CysProAsn ProGlyGluI leArgAsnGl yGlnIleAsp ValProGlyGly
         130                                    140                                    160
                                                nlaIII           rsaI
                                                CATGTAACAC AGGGTACAAA
601 GCATATTATT TGGTGCAACC ATCTCCTTCT CATGTAACAC AGGGTACAAA
    CGTATAATAA ACCACGTTGG TAGAGGAAGA GTACATTGTG TCCCATGTTT
    IleLeuPh eGlyAlaThr IleSerPheS erCysAsnTh rGlyTyrLys
         150                                                                              160
               taqI                             aluI
                                                fnu4HI
                                                bbvI
    TTATTTGGCT CGACTTCTAG TTTTTGTCTT ATTTCAGGCA GCTCTGTCCA
    AATAAACCGA GCTGAAGATC AAAAACAGAA TAAAGTCCGT CGAGACAGGT
    LeuPheGlyS erThrSerSe rPheCysLeu IleSerGlyS erSerValGln
                                    170
701 GTGGAGTGAC CCGTTGCCAG AGTGCAGAGA AATTTATTGT CCAGCACCAC
    CACCTCACTG GGCAACGGTC TCACGTCTCT TTAATAATAA GGTCGTGGTG
    TrpSerAsp ProLeuProG luCysArgI uIleTyrCys ProAlaProPro
         180                                    190
    CACAAATTGA CAATGGAATA ATTCAAGGGG AACGTGACCA TTATGGATAT
    GTGTTTAACT GTTACCTTAT TAAGTTCCCC TTGCACTGGT AATACCTATA
    GlnIleAs pAsnGlyIle IleGlnGlyG luArgAspHi sTyrGlyTyr
              nsiI                                              210
              avaI                  hphI       nlaIII
                                    hinfI     nlaIII           hgiAI
                                                                bsp1286
801 AGACAGTCTG TAACGTATGC ATGTAATAAA GGATTCACCA TGATTGGAGA
    TCTGTCAGAC ATTGCATACG TACATTATTT CCTAAGTGGT ACTAACCTCT
    ArgGlnSerV alThrTyrAl aCysAsnLys GlyPheThrM etIleGlyGlu
                        200                                    220
                                                               sau96I
                                                               haeIII
    GCACTCTATT TATTGTACTG TGAATAATGA TGAAGGAGAG TGGAGTGGCC
    CGTGAGATAA ATAACATGAC ACTTATTACT ACTTCCTCTC ACCTCACCGG
    HisSerIle TyrCysThrV alAsnAsnAs pGluGlyGlu TrpSerGlyPro
         230                                                   240
```

Fig.2d.

```
                          sau96I
                          nlaIV
              bsmI            mnlI                 styI                                    avaII
 901 CACCACCTGA ATGCAGAGGA AAATCTCTAA CTTCCAAGGT CCCACCAACA
     GTGGTGGACT TACGTCTCCT TTTAGAGATT GAAGGTTCCA GGGTGGTTGT
     ProProGl uCysArgGly LysSerLeuT hrSerLysVa lProProThr
                  250                                            260
                                                                      hphI
     GTTCAGAAAC CTACCACAGT AAATGTTCCA ACTACAGAAG TCTTACCAAC
     CAAGTCTTTG GATGGTGTCA TTTACAAGGT TGATGTCTTC AGAGTGGTTG
     ValGlnLysP roThrThrVa lAsnValPro ThrThrGluV alSerProThr
                                            270
           ddeI                                                           CAAGCAACAC
1001 TTCTCAGAAA ACCACCACCA AAACCACCAC ACCAAATGCT CAAGCAACAC
     AAGAGTCTTT TGGTGGTGGT TTTGGTGGTG TGGTTTACGA GTTCGTTGTG
     SerGlnLys ThrThrThrL ysThrThrTh rProAsnAla GlnAlaThrArg
         280                                            290
         scrFI                                       nlaIII
         bstNI                                        mboII
      rsaI                                          rsaI
     GGAGTACACC TGTTTCCAGG ACAACCAAGC ATTTTCATGA ACCCGTCTTC TATCTGGTTC
     CCTCATGTGG ACAAAGGTCC TGTTGGTTCG TAAAAGTACT TGGGCAGAAG ATAGACCAAG
     SerThrPr oValSerArg ThrThrLysH isPheHisGl uThrArgLeu euSerGlySer
                 300                                                 310
            xmnI
            nlaIV
1101 AATAAAGGAA GTGGAACCAC TTCAGGTACT ACCCGTCTTC TATCTGGTTC
     TTATTTCCTT CACCTTGGTG AAGTCCATGA TGGGCAGAAG ATAGACCAAG
     AsnLysGlyS erGlyThrTh rSerGlyThr ThrArgLeuL euSerGlySer
                                            320
           hphI    scrFI                    sau3AI           aluI  pstI
                    bstNI                    dpnI            AGCTCACTGC
     TCGTCCTGTC ACCCAGGCTG GTATGCGGTG GTGTGATCGT AGCTCACTGC
     AGCAGGACAG TGGGTCCGAC CATACGCCAC CACTACTAGCA TCGAGTGACG
     ArgProVal ThrGlnAlaG lyMetArgTr pCysAspArg SerSerLeuGln
        330                                              340
         taqI       sau3AI                                   bstXI
                     dpnI                                     mnlI
1201 AGTCTCGAAC TCCTGGGTTC AAGCGATCCT TCCACTTCAG CCTCCCAAGT
     TCAGAGCTTG AGGACCCAAG TTCGCTAGGA AGGTGAAGTC GGAGGGTTCA
     SerArgTh rProGlyPhe LysArgSerP heHisPheSe rLeuProSer
                    350                                     360
     aluI rsaI  bsp1286                    hincII              hgaI
     AGCTGGTACT ACAGGCACA CGTGTTTCAC GTTGACAGGT TTGCTTGGGA
     TCGACCATGA TGTCCGTGT GCACAAAGTG CAACTGTCCA AACGAACCCT
     SerTrpTyrT yrArgAlaHi sValPheHis ValAspArgP heAlaTrpAsp
                                    370
```

Fig. 2e.

```
                 nlaIII
            styI
            ncoI                        ddeI             mboII
1301 CGCTAGTAAC CATGGGCTTG CTGACTTAGC CAAAGAAGAG TTAAGAAGAA
     GCGATCATTG GTACCCGAAC GACTGAATCG GTTTCTTCTC AATTCTTCTT
     AlaSerAsn HisGlyLeuA laAspLeuAl aLysGluGlu LeuArgArgLys
                380                              390
             accI                      ddeI
     AATACACACA AGTATACAGA CTGTTCCTAG TTTCTTAGAC TTATCTGCAT
     TTATGTGTGT TCATATGTCT GACAAGGATC AAAGAATCTG AATAGACGTA
     TyrThrGl nValTyrArg LeuPheLeuV alSerAM*
                400
                                 mboII
                           hgiAI               sfaNI
                           bsp1286              fokI
1401 ATTGGATAAA ATAAATGCAA TTGTGCTCTT CATTAGGAT GCTTTCATTG
     TAACCTATTT TATTTACGTT AACACGAGAA GTAAATCCTA CGAAAGTAAC
                           hincII
     TCTTTAAGAT GTGTTAGGAA TGTCAACAGA GCAAGGAGAA AAAGGCAGT
     AGAAATTCTA CACAATCCTT ACAGTTGTCT CGTTCCTCTT TTTTCCGTCA
     hinfI
     scrFI            ddeI                  mnlI
     bstNI
1501 CCTGGAATCA CATTCTTAGC ACACCTACAC CTCTTGAAAA TAGAACAACT
     GGACCTTAGT GTAAGAATCG TGTGGATGTG GAGAACTTTT ATCTTGTTGA
                    hinfI
     TGCAGAATTG AGAGTGATTC CTTTCCTAAA AGTGTAAGAA AGCATAGAGA
     ACGTCTTAAC TCTCACTAAG GAAAGGATTT TCACATTCTT TCGTATCTCT
            sau3AI
            dpnI  mnlI
1601 TTTGTTCGTA TTTAGAATGG GATCACGAGG AAAAGAGAAG GAAAGTGATT
     AAACAAGCAT AAATCTTACC CTAGTGCTCC TTTTCTCTTC CTTTCACTAA
```

Fig.2f.

```
          sau3AI
          dpnI
          xhoII
          bglII
     TTTTCCACA AGATCTGTAA TGTTATTCC ACTTATAAAG GAAATAAAAA
     AAAAAGGTGT TCTAGACATT ACAATAAAGG TGAATATTTC CTTTATTTTT
                                                            mboII
              ecoRV
1701 TGAAAAACAT TATTTGGATA TCAAAAGCAA ATAAAACCCA ATTCACTCTC
     ACTTTTTGTA ATAAACCTAT AGTTTTCGTT TATTTTGGGT TAAGTCAGAG
     ddeI
     TTCTAAGCAA AATTGCTAAA GAGAGATGAA CCACATTATA AAGTAATCTT
     AAGATTCGTT TTAACGATTT CTCTCTACTT GGTGTAATAT TTCATTAGAA
                                                   draI
                                              sspI ahaIII
1801 TGGCTGTAAG GCATTTTCAT CTTTCCTTCG GGTTGGCAAA ATATTTTAAA
     ACCGACATTC CGTAAAAGTA GAAAGGAAGC CCAACCGTTT TATAAAATTT
            nlaIII hphI  scrFI
                         bstNI                 hphI       mnlI
     GGTAAACATG CTGGTGAACC AGGGGTGTTG ATGGTGATAA GGGAGGAATA
     CCATTTGTAC GACCACTTGG TCCCCACAAC TACCACTATT CCCTCCTTAT
               mboII
          hinfI
1901 TAGAATGAAA GACTGAATCT TCCTTGTTGC ACAAATAGAG TTTGGAAAAG
     ATCTTACTTT CTGACTTAGA AGGAACAACG TGTTTATCTC AAACCTTTTC
                                      draI
          mboII                        ahaIII
     CCTGTGAAAG GTGTCTTCTT TGACTTAATG TCTTTAAAAG TATCCAGAGA
     GGACACTTTC CACAGAAGAA ACTGAATTAC AGAAATTTTC ATAGGTCTCT
                                                     taqI
       sspIpI                                       hinfI
2001 TACTACAATA TTAACATAAG AAAAGATTAT ATATTATTTC TGAATCGAGA
     ATGATGTTAT AATTGTATTC TTTTCTAATA TATAATAAAG ACTTAGCTCT
                                            sspI
     TGTCCATAGT CAAATTTGTA AATCTTATTC TTTTGTAATA TTTATTTATA
     ACAGGTATCA GTTTAAACAT TTAGAATAAG AAAACATTAT AAATAAATAT
           nlaIII
2101 TTTATTTATG ACAGTGAACA TTCTGATTTT ACATGTAAAA CAAGAAAAGT
     AAATAAATAC TGTCACTTGT AAGACTAAAA TGTACATTTT GTTCTTTTCA
```

```
          mboIII
       mboII           mboII
       TGAAGAAGAT ATGTGAAGAA AAATGTATTT TTCCTAAATA GAAATAAATG
       ACTTCTTCTA TACACTTCTT TTTACATAAA AAGGATTTAT CTTTATTTAC
       sau3AI                                      sau3AI
       dpnI                                        dpnI
2201   ATCCCATTTT TTGGTAAAAA AAAAAAAAAA AAA
       TAGGGTAAAA AACCATTTT  TTTTTTTTTT TTT
```

Fig. 2g.

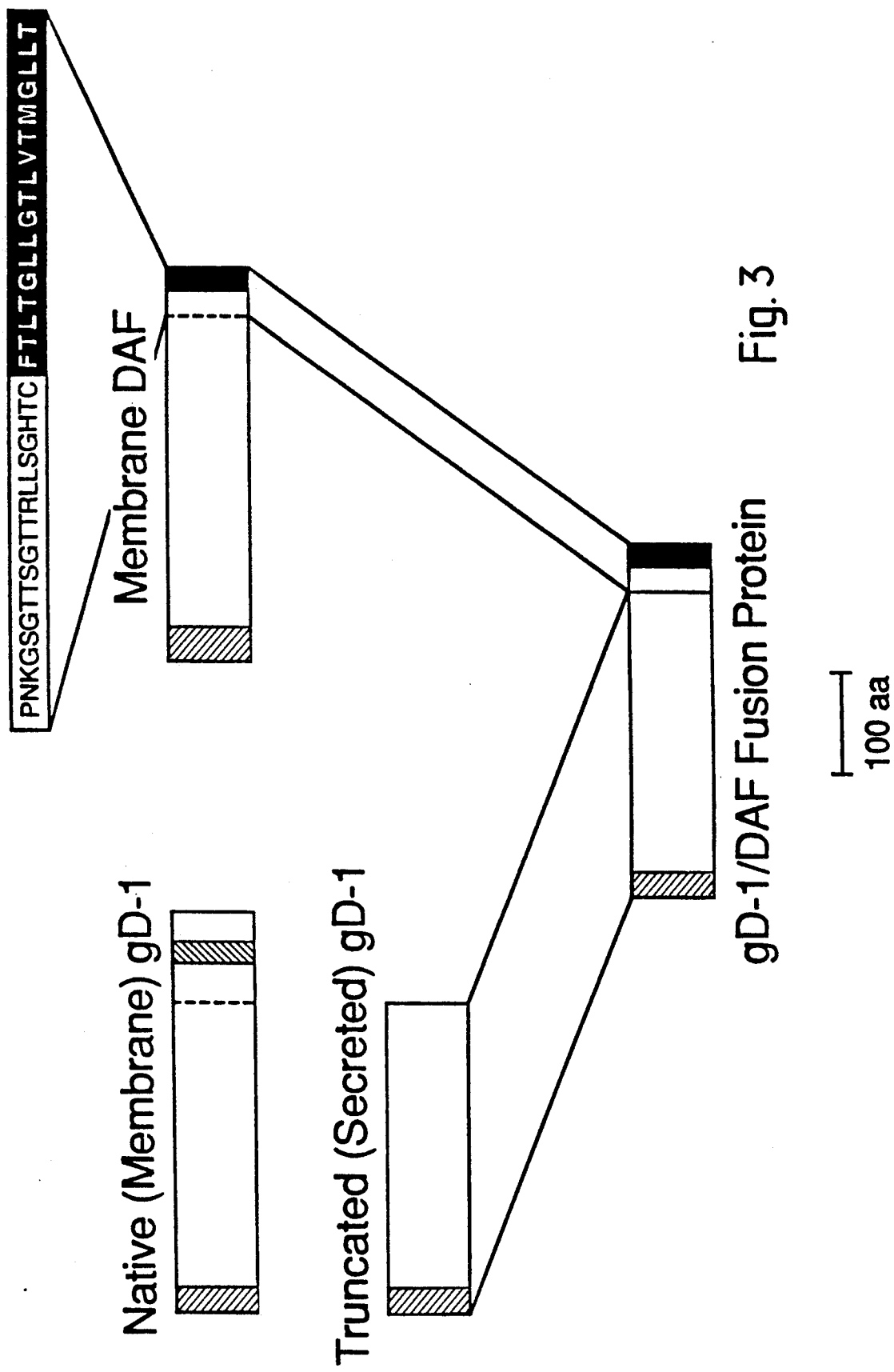

NUCLEIC ACIDS VECTORS AND CELLS FOR THE SYNTHESIS OF MEMBRANE ANCHOR FUSION POLYPEPTIDES

This is a divisional of U.S. Ser. No. 07/083,757, filed Aug. 6, 1987 now U.S. Pat. No. 5,109,113, which is continuation-in-part of U.S. Ser. No. 06/859,107, filed May 2, 1986 (Abandoned); U.S. Ser. No. 06/738,171 filed May 24, 1985 (Abandoned); and PCT/US86/01177 filed May 23, 1986 (Abandoned).

This application relates to the preparation of decay accelerating factor (hereinafter abbreviated as DAF) in recombinant cell culture. In particular, it is concerned with the large scale manufacture of DAF suitable for pharmaceutical or diagnostic use.

Antigenic cells targeted by the humoral immune response are lysed by a process called complement activation. This process consists of a series or cascade of proteolytic activities initiated by the binding of antibody with its antigen. The components that participate in complement activation are many and complex, although for the purposes herein the most important are C4b and C3b. In a key step in complement activation, these two proteins become covalently associated with the target cell surface and then serve as anchors for the assembly of C3 and C5 convertases, the amplifying enzymes of the cascade.

Complement activation must focus only on the target and must not occur on host cells. However, in the course of complement activation, large numbers of nascent C4b and C3b fragments are liberated into the fluid phase. Most react with water, but some by chance could bind to nearby host cells and lead to their damage. For this and possibly other reasons, the activities of bound, as well as free, C3b and C4b fragments are under strict control by a complex system of serum and membrane proteins.

Recent evidence (Medof, et al. 1982. "J. Exp. Med." 156:1739; Medof et al. 1984. "J. Exp. Med." 159:1669) suggests that regulation of the activities of substrate-bound C4b and C3b is distinct from control of the fluid phase fragments. The functions of the former are controlled mainly by two membrane proteins: the C3b/C4b receptor (CR1) and DAF. CR1 dissociates C2 and factor B from C4b and C3b in C3 and C5 convertase complexes and promotes the cleavage of C3b (Medof, et al. 1982. "J. Exp. Med." 156:1739; Fearon, D. T. 1979, "Proc. Natl. Acad. Sci. USA" 76:5867; Medicus, et al. 1983. "Eur. J. Immunol." 13:465; and Ross, et al. 1982 "J. Immunol." 129:2051) and C4b (Medof, et al. 1984. "J. Exp. Med." 159:1669; Iida et al. 1981. "J. Exp. Med." 153:1138) by the serum enzyme C3b/C4b inactivator (I). DAF has been shown also to enhance the decay dissociation of C2 and factor B from C3 convertases (Nicholson-Weller, et al. 1982, "J. Immunol." 129:205 and Pangburn, M. K. et al. 1983 "J. Exp. Med." 157:1971). The reason for the apparent redundancy in regulatory activities of the two membrane factors and their respective roles in convertase control has remained unclear. Abnormalities of CR1 have been found in systemic lupus erythematosus (SLE) (Miyakawa, Y. et al. 1981 "Lancet" 2:493; Iida, K. et al. 1982 "J. Exp. Med." 155:1427; Wilson, J. G. et al. 1982 "N. Engl. J. Med." 307:981; Taylor, R. P. et al. 1983 "Arthritis Rheum." 26:736), a condition associated with defective immune complex handling, and abnormalities of DAF have been found in paroxysmal nocturnal hemoglobinuria (PNH) (Pangburn, M. K. et al. 1983 "J. Exp. Med." 157:1971; Pangburn, M. K. et al. 1983 "Proc. Natl. Acad. Sci." 80:5430; Nicholson-Weller, A. et al. 1983 "Proc. Natl. Acad. Sci." 80:5066), a condition associated with heightened susceptibility of blood cells to lysis.

DAF was reported to have been purified to a single 70 Kd band on silver stained SDS-PAGE from a pooled extract of human erythrocytes stroma (Medof et al., 1984, "J. Exp. Med." 160:1558). The molecule was hydrophobic and tended to form multimers of $\geq 150$ Kd as determined by molecular sieve chromatography. Purified DAF could reassociate with red blood cells. Only a small number of DAF molecules ($<10$) had a significant effect on the hemolytic effect of activated complement. Medof et al. concluded that DAF can only function intrinsically within the cell membrane, and suggested that it offered the possibility of correcting in vitro the defect in the membranes of cells from patients with PNH.

Existing methods for obtaining DAF are unsatisfactory for its commercial preparation. Red cells contain extremely small quantities of DAF. Furthermore, blood contains viruses and other biologically active components which pose a risk of adverse reactions in recipients or users.

Red blood cell DAF is limited to the native membrane bound form, including any naturally occurring alleles as may exist. Methods are needed for synthesizing amino acid and glycosylation variants which can function as DAF agonists characteristics such as the absence of C-Terminal lipid, resistance to proteases, or the ability to deliver DAF to the membranes of target cells.

Accordingly, it is an object herein to prepare DAF in commercial quantity from a therapeutically acceptable source.

It is a further object to obtain human DAF from a source that is completely uncontaminated with other human proteins.

It is an additional object to prepare amino acid sequence and glycosylation variants of DAF.

Other objects of this invention will be apparent from the specification as a whole.

SUMMARY

The objects of this invention are accomplished by expression of DAF in recombinant cell culture, a process that fundamentally comprises providing nucleic acid encoding DAF, transforming a host cell with the DAF-encoding nucleic acid, and culturing the cell in order to express DAF in the host cell culture.

The method of this invention enables the preparation of novel forms of DAF, including amino acid sequence variants and glycosylation variants. Amino acid sequence variants consist of deletions, substitutions and insertions of one or more DAF amino acid residues. DAF also is expressed in a form unaccompanied by the glycosylation associated with the native DAF (including unaccompanied by any glycosylation whatsoever), obtained as a product of expression of DAF in heterologous recombinant cell culture. DAF in any form as a component of a recombinant cell culture is novel.

Unexpectedly, we discovered during our studies of cell processing of DAF mRNA that the membrane-bound form of DAF (mDAF) is not the only form in which it is expressed in vivo. In fact another form of DAF exists, called sDAF. This form is encoded by an mRNA species from which the last 3' intron has not been spliced, resulting in an amino acid sequence C-terminal to residue 327 that is entirely different from that of mDAF. The novel C-terminus of sDAF is postulated to result in vivo in the secretion of the protein into the blood stream (where it may be biologically active) because the presence of the intron changes the reading frame of the last exon so as to eliminate the "signal" directing attachment of phosphatidylinositol (the membrane anchor for mDAF). This novel form of DAF was unappreciated until the pioneering work herein was accomplished, and it differs from mDAF in containing an antigenically distinct C-terminus. sDAF is useful in diagnosis of PNH since it is now possible to determine whether the condition in an individual results from a failure to express any of the DAF gene or a failure of post-translational processing to attach the phosphatidylinositol anchor.

Novel nucleic acids also are provided, including (1) cell free nucleic acid identified as encoding DAF, including genomic DNA, cDNA or RNA, I2) DNA encoding DAF free of an untranslated intervening sequence (introns) or flanking genomic DNA, and (3) nucleic acid encoding DAF which is free of nucleic acid encoding any other protein homologous to the source of the nucleic acid that encodes DAF. Also within the scope of this invention is nucleic acid which does not encode DAF but which is capable of hybridizing with nucleic acid encoding DAF.

Nucleic acid encoding DAF is useful in the expression of DAF in recombinant cell culture or for assaying test samples for the presence of DAF-encoding nucleic acid. Labelled DAF-encoding or hybridizing nucleic acid is provided for use in such assays.

Recombinant DAF is formulated into therapeutically acceptable vehicles and administered for the treatment of PNH or inflammatory or cell lytic autoimmune diseases. DAF conjugates or fusions are prepared that deliver DAF to target cells in order to inhibit complement activation at the surfaces of such cells. The conjugates or fusions are useful for ameliorating allograft rejection or autoimmune diseases.

The glycophospholipid membrane anchor domain for mDAF, or functionally equivalent domains from other proteins which also are anchored by glycophospholipids, are fused to proteins or multimers of such proteins which are heterologous to the source of the membrane anchor domain, for example hormones, antigens (especially from infectious organisms), allergens, immunoglobulins, enzymes, receptors and the like. The anchor fusions are used in combination with the recombinant cells which express them or are recovered and formulated into therapeutic compositions, used as diagnostic assay components, or employed in affinity purification procedures. The fusions will contain the heterologous polypeptide fused at its C-terminus to the anchor domain, which in turn is covalently substituted at its C-terminal carboxyl with a glycophospholipid.

BRIEF DESCRIPTION OF THE DRAWINGS

FIGS. 1a-2c (Seq. ID No. 9) depict the cDNA sequence for clones λ33 (to the HindIII site at residue 1) and λ47 (HindIII to the 3' end). The point at which the intron is removed is designated by an asterisk. The probable phosphatidylinositol derivatization site is $Cys_{330}$ and the C-terminal hydrophobic region extends from residues 331-347. Amino acid residues are numbered from the mature amino terminus at $Asp^1$.

FIGS. 2a-2c (Seg. ID No. 10) depict the cDNA sequence of clones λ33 to the HindIII site at residue +1) and λ41 (HindIII to 3' end) encoding human sDAF. The unspliced intron in the cDNA encoding sDAF is bracketed. Restriction enzyme sites are shown using conventional abbreviations. The predicted amino acid sequence for each DAF predicted species is shown, together with the secretory leader and mature N-terminus of each (designated by arrows).

FIG. 3 is a schematic diagram showing the regions of HSV 1 glycoprotein D (gD-1) and DAF that are present in the gD-1/DAF fusion protein produced in Example 3. Truncated (secreted) gD-1 was constructed from native (membrane) gD-1 (14) and comprises amino acids 1-300, including the hydrophobic signal sequence (residues 1-25, indicated as a gray area). The hydrophobic membrane spanning domain (residues 340-360, cross-hatched region) and the C-terminal hydrophobic domain (residues 361-393) are excluded. The point of truncation (residue 300) is indicated by a broken line. Truncated gD-1 was fused to residue 311 of membrane DAF. the gD-1/DAF fusion contains the last 37 residues of membrane DAF predicted from the cDNA sequence (residues 311-347) and includes a C-terminal hydrophobic region (residues 331-347, depicted in black).

DETAILED DESCRIPTION

Figure 2A:
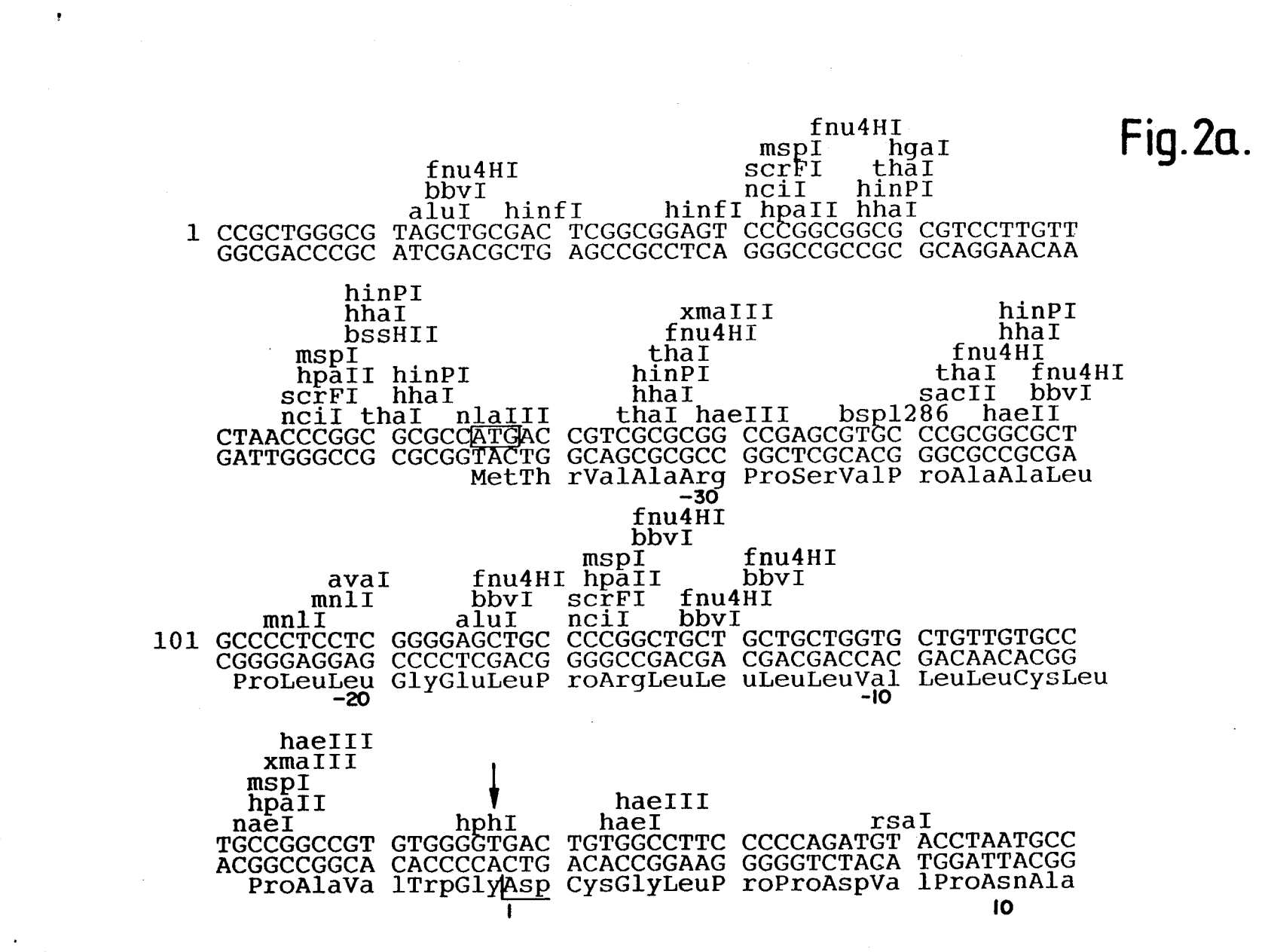

DAF is defined to be any molecule having the pre or mature amino acid sequence set forth in FIGS. 1 or 2 as well as their amino acid sequence or glycosylation variants (including natural alleles) which are capable of exhibiting a biological activity in common with the native DAF of FIGS. 1 or 2. Henceforth, the term DAF shall mean either or both forms unless otherwise appropriate. Native DAF is DAF obtained from serum, blood cells or other animal fluids or tissues. DAF biological activity is defined as any of 1) immunological cross-reactivity with at least one epitope of native DAF, or 2) the possession of at least one hormonal, regulatory or effector function qualitatively in common with native DAF. Since amino acid sequence variations of DAF having antagonist or agonist activity are included, an amino acid sequence variant need not exhibit any DAF immunomodulatory activity to fall within the definition of DAF. For example, a variant may act as an antagonist and competitively inhibit native DAF, yet have no immunomodulatory activity per se. Alternatively, the variant may be neither an antagonist nor have immunomodulatory activity, but still fall within the definition if it remains capable of cross-reacting with antibody raised against native DAF. An example of a presently known DAF immunomodulatory activity is inhibition of C4b2a functional activity (Medof et al., 1984, Id.).

Amino acid sequence variants of DAF include deletions from, or insertions or substitutions of residues within the pre or mature DAF sequence shown in FIGS. 1 or 2. Amino acid sequence deletions generally range from about 1 to 10 residues and typically are contiguous. Contiguous deletions ordinarily are made in even numbers of residues, but single or odd numbers of deletions ar e within the scope hereof. Representative deletions are [des $Cys_{33}$] mature mDAF, [des $Cys_{330}$ - $Thr_{347}$] mature mDAF, [des $Thr_2$ - $Gly_{327}$] mature sDAF. A particularly interesting deletion is $Cys_{330}$-$Thr_{347}$ from mDAF. This eliminates the membrane anchor site and transmenbrane region, resulting in a molecule that, like sDAF, is secreted but which bears none of the unique antigenic determinants of sDAF.

Insertions also are preferably made in even numbers of residues when the variation falls within the mature DAF sequence, although insertions may range from 1 to 5 residues in general. However, insertions also include fusions onto the amino or carboxyl termini of DAF or from 1 residue to polypeptides of essentially unrestricted length. An example of a single terminal insertion is mature DAF having an N-terminal methionyl. This variant is an artifact of the direct expression of DAF in recombinant cell culture, i.e., expression without a signal sequence to direct the secretion or cell membrane association of mature DAF. Other examples of terminal insertions include 1) fusions of heterologous signal sequences to the N-terminus of mature DAF in order to facilitate the secretion of mature DAF from recombinant hosts, 2) fusions of immunogenic polypeptides, e.g. bacterial polypeptides such as beta-lactamase or an enzyme encoded by the $E.\ coli$ trp locus and 3) fusions with cell surface binding substances, including hormones, growth factors or antibodies. Fusions with cell surface binding substances need not be produced by recombinant methods, but can be the product of covalent or noncovalent association with DAF, including its phosphatidylinositol group. For example, an antibody or fragment thereof bearing the variable region is covalently bound to, or expressed in recombinant cell culture as a fusion with, the C-terminus of DAF. For amelioration of allograft rejection the DAF is bound to antibodies specific for the HLA antigens of the allograft. The antibody and DAF are covalently bounded, for example, by the method of EP 170,697A, although other methods for linking proteins are conventional and known to the artisan. Immunogenic fusions are useful for preparing immunogenic DAFs suitable as vaccines for preparing anti-DAF antibodies. These are useful for the preparation of diagnostic reagents. Representative insertions are [Thr$_{329}$ Leuleu Cys$_{330}$] (Seq. ID No. 1) mature DAF, [Arg$_{100}$ His Arg$_{100}$] mature DAF, [Lys$_{125}$ GlnLys$_{126}$ GlnLys$_{127}$] (Seq. ID No. 2) mature DAF, [Pro$_{193}$LeuLeu Ala$_{194}$] (Seq. ID No. 3) mature DAF, [Pro$_{247}$ AspAspGlu$_{248}$] (Seq. ID No. 4) mature DAF, [Thr$_{282}$SerSerThr$_{283}$] (Seq. ID No. 5) mature DAF, and [Gly$_{316}$ ThrThrThr$_{317}$] (Seq. ID No. 6) mature DAF.

The third group of variants are those in which at least one residue in the DAF molecule has been removed and a different residue inserted in its place. Such substitutions generally are made in accordance with following Table.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg; gly; glu |
| Met | met; leu; tyr |
| Ser | thr |
| Thr | ser |
| Trp | tyr |
| Tyr | trp; phe |

TABLE 1-continued

| Original Residue | Exemplary Substitutions |
| --- | --- |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet of helical conformation, (b) the charge or hydrophobicity of the molecule at the target site or (c) the bulk of the side chain. The substitutions in general expected to produce the greatest changes in DAF properties will be those in which (a) a hydrophilic residue, e.g. seryl or threonyl, is substituted for (or by) a hydrophobic residue, e.g. leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having such a side chain, e.g. glycine.

Representative substituted DAFs are [Cys$_{330}$→Met] mature mDAF, [Cys$_{330}$→Ser] mature mDAF, [Cys$_2$→Ser] mature mDAF, [Lys$_{125}$ Lys$_{126}$→Gln] mature DAF, [Gly$_{144}$→Pro] mature DAF, [Ile$_{146}$→Met] mature DAF, [Phe$_{169}$→Tyr] mature DAF, [Pro$_{192}$→Gly] mature DAF, [Ile$_{201}$→Leu] mature DAF, [Asn$_{236}$Asn$_{237}$→AspAsp] mature DAF, [Glu$_{239}$→Asp] mature DAF, [Ser$_{256}$→Tyr] mature DAF, [Val$_{268}$→Phe] mature DAF, [Lys$_{285}$→Gln] mature DAF, [Thr$_{294}$→Ser] mature DAF and [Leu$_{324}$→Ser] mature DAF.

The above described variants are made in either sDAF or mDAF. The following variants are made in the unique sDAF C-terminal: [Lys$_{352}$→Gln] mature sDAF, [Cys$_{339}$→Ser] mature sDAF, [Arg$_{394}$→His] mature sDAF and mature sDAF [Leu$_{403}$ Phe$_{404}$ Leu$_{405}$→SerTyrSer] mature sDAF.

for the purposes herein, any naturally occurring alleles are not included within the scope of DAF variants because the variants described herein are predetermined DAF variants.

The C-terminal domain of mDAF contains a site (referred to as the "phospholipid anchor domain") to which phospholipid, generally glycophospholipid, is attached in the course of post-translational processing. This domain contains about from 20-30 residues, the phospholipid bding covalently linked to the C-terminal residue corboxyl. This domain or any fragment of mDAF containing it, is produced as a fusion with any other polypeptide for which it is desired to create a membrane-bound form. It will be understood that "phospholipid anchor domain" when used in reference to expressed fusions refers to the post-translationally modified fusion, as will be described more fully infra. For example, an ordinarily secreted hormone is produced in recombinant cell culture as a C-terminal fusion of the preprotein with the phospholipid anchor domain of mDAF. Rather than being secreted this fusion will be transported to the cell membrane and remain lodged there by virtue of the phosphatidy-choline anchor. Such recombinant cells are useful as immunogens or vaccines for the hormone or other selected polypeptide. Sequestering the polypeptide in the membrane also protects it from dilution into the culture medium. Finally, fusion polypeptides having C-terminal lipids are useful in diagnostic assays for the polypeptides or their antibodies since the terminal lipid provides a convenient site for adsorption onto microtiter or test tube surfaces and the like.

Other proteins are known that contain C-terminal domains substituted with phospholipid anchors. Such proteins include Thy-1 (Low et al., "Nature" (London) 318:62 [1985] and Tse et al., "Science" 230:1003 [1985]), the variant surface glycoproteins (VSGs) of African trypanosomes (Ferguson et al., "J. Biol. Chem." 260:14547 [1985]), acetylcholinesterase (Futerman et al., "Biochem. J." 226:369 [1985]), 5' nucleotidase (Low et al., "Biochim. Biophys. Acta" 508:565 [1978]) as well as DAF (Davitz et al., "J. Exp. Med." 163:1150 [1986] and Medof et al., "Biochemistry" 25:6740 [1986]). Attachment of the DAF anchor, which contains glycosylated phosphatidylinositol (PI) and ethanolamine, apparently occurs following proteolytic removal of 17-31 C-terminal residues from mDAF (Low, M. G. "J. Biochem." 244:1-13 [1987] and Cross, G. A. M., "Celol"48:1-79-181 [1987]).

In order to construct fusions of a desired polypeptide and a phospholipid anchor domain, DNA encoding the C-terminal about 30-50 residues of a polypeptide ordinarily bearing such an anchor is ligated to DNA encoding the desired polypeptide, or to a suitable fragment multimer or amino acid sequence variant thereof. The DNA encoding the anchor recognition site is inserted at the C-terminus of the desired protein. The anchor recognition site includes the anchor domain as well as a short, approximately 10-20 residue, hydrophobit sequence located C-terminal to the anchor domain which will be processed off the fusion. This is accomplished by routine procedures well known to those skilled in the art. For example, the DNA encoding the selected phospholipid anchor recognition site is synthesized by in vitro methods or by obtaining a suitable fragment from cDNA or genomic DNA encoding the native anchored protein. Since the anchor domain is found within the about from 20 to 40 residues upstream from the C-terminal hydrophobic domain one should use DNA encoding the hydrophobic domain as well as the approximately 20 to 40 residues upstream therefrom.

Many proteins in addition to DAF are known to contain glycophospholipid anchors, and their amino acid sequences (including the C-terminal about 20-50 residues which will be employed as anchors in heterologous fusions) are known. Examples include acetylcholinesterase (M. Schumacher et al., "Nature" 319:407-409 [1986]), Thy-1 (T. Seki et al., "Nature" 313:485-487 [1985] and T. Moriuchi et al. "FEBS Lett." 178:105-108 [1985]), VSG (T. Brucei) (Cross, "Philos. Trans. R. Soc. London" Ser. B 307:3-12 [1984]) and alkaline phosphatase (Weiss et al., "Proc. Natl. Acad. Sci. USA" 83:7182-7186 [1986]). For general reviews on such polypeptides see M. G. Low, "Biochem. J." 244:1-13 (1987) and M. G. Low et al. "TIBS" 11:212-215 (1986).

In some instances, e.g. where the C-terminus of the heterologous polypeptide contains an active site or immune epitope which is to be sterically free, then it will be desirable to introduce a spacer polypeptide between the C-terminus of the heterologous polypeptide and the phospholipid anchor domain. This optimally will be additional sequences from the anchor domain donor polypeptide, for example about from 10 to 50 residues N-terminal to the anchor domain, but also may be artificial sequences.

The amino acid sequences inputed from DNAs encoding phospholipid anchor domains exhibit little or no sequence homology beyond a C-terminal sequence of about from 10 to 20 residues containing uncharged, hydrophobic residues (leucine, glycine, threonine, valine, methionine, isoleucine and/or phenylalanine). However, this notwithstanding, the phospholipid anchor domain is embraced with the region immediately N-terminal to the hydrophobic sequence and is readily identifiable on this basis. Those skilled in the art will be capable of refining the optional sequence of the phospholipid anchor domain.

As noted above, the character and identity of polypeptides to be linked to the phospholipid anchor domain are unlimited. Their choice will depend upon the therapeutic or diagnostic objection which is intended. All that is necessary is that the fused polypeptide exhibit the desired biological activity of the unfused polypeptide prior to its expression as a hybrid with a phospholipid anchor domain. The polypeptide may be of any length, from about 4 residues to thousands, and includes enzymes, hormones, antigens and the like.

The expression hosts for these fusions are cells capable of processing the phospholipid recognition site and attaching the phospholipid to the anchor domain. Such cells preferably are mammalian continuous cell lines as described elsewhere herein, most preferably DHFR− CHO cells.

The fused polypeptide is employed together with the cells in which it is produced, i.e., without recovery from the expression hosts, in the immunogen utility described above. In other instances, e.g. adsorption of the fusion to hydrophobic affinity matrices in connection with preparing diagnostic kits, the fusion is recovered from the expression host prior to its use. The fusion is recovered from host cell membranes by preparing cell membrane extracts in substantially the same fashion as mDAF or other anchored polypeptides heretofore have been isolated. Other methods for obtaining preparations of membrane anchored polypeptides such as receptors also are known and are adaptable for use in recovering the fusions described herein. Typically, the host cell membranes are separated from the cytoplasm, solubilized with nonionic detergent, and the fusion recovered by adsorption on immunoaffinity, substrate or ligand affinity columns. The fusions will be recovered as polypeptides containing the heterologous polypeptide and glycophospholipid anchor domain together with C-terminally linked glycophospholipid. Note that the fusion protein will be recovered in a form which is free of the C-terminal hydrophobic sequence present before processing of the fusion and substitution with the glycophospholipid.

Fusions which are purified free of host cell membranes are useful as therapeutic compositions. For example, a fusion containing a plasminogen activator enzyme such as urokinase or tissue plasminogen activator is fused to a glycophospholipid anchor domain and administered in therapeutic compositions to patients experiencing myocardial infarcts or other disorders accompanied by undesirable blood clots. Preferably, the enzyme is fused at its C-terminus to the N-terminus of the glycophospholipid anchor domain. It will be understood that "glycophospholipid anchor domain" includes both the amino acid sequence as well as the glycophospholipid substituted at a carboxyl group of the C-terminal amino acid residue. The fused plasminogen activator will insert into blood cells and vasculature where it will be most effective at activating plasminogen and will not be subject to removal from the blood stream by degradative processes such as those performed by the liver or spleen, thereby extending the half life of the enzyme and targeting it more directly to the desired therapeutic site.

These advantages are applicable to any polypeptide which desirably functions at cell membrane surfaces, particularly cells readily accessible to the circulatory system such as hematopoietic cells or vascular epithelia. For example, patients suffering from disorders characterized by the absence of a critical enzyme activity, as for example in inborn errors of metabolism, are treated by an infusion of the enzyme in question fused to a phospholipid anchor domain. The kinetics of synthesis and delivery to the cells of the required metabolite are improved over simply infusing the metabolite. This approach also provides many advantages over somatic cell transformation as an alternative method to providing the metabolite. The fusion is injected into the cerebrospinal fluid, e.g., in order to address metabolic deficiencies of brain cells, or into the lymph system or blood stream as required to optimally target other tissue or organ system-specific disorders.

The novel fusions are particularly useful in overcoming defects or deficiencies within the immune system, particularly in the process of antigen presentation. An antigen to which it is desired to modulate an immune response is synthesized as a fusion with a phospholipid anchor domain and fusion administered under conditions and in a dosage determined to produce the desired effect. There is no limit on the choice of antigen, but the fusion must preserve the relevant epitope(s) of the antigen. This is readily determined by conventional competitive-type immunoassay using antibody raised against the native antigen and labeled native antigen, in accordance with methods well known to those skilled in the art. Antigen fusions also are useful in in vitro diagnostics as described above or in affinity chromatography.

The novel fusions herein optionally are formulated into liposomes or other lipid membrane carriers. This is readily accomplished by mixing a solution of the fusion with a preformed liposomal suspension and incubating until the insertion of the fusions into the liposomal bilayer. Alternately, the fusions are admixed with the aqueous solution used in the preparation of the liposomes. Alternatively, the fusions are formulated into conventional pharmacologically acceptable vehicles as described below for mDAF. Since the fusions bear hydrophobic substituent they can be formulated with pharmacologically acceptable detergents such as Tween 20 or PEG, or with serum albumin.

The following disclosure relating to DAF is to be considered as applying with equal effect to the glycophospholipid fusions described immediately infra, except as noted that the fusions should be produced in higher eukaryotes.

Most deletions and insertions, and substitutions in particular will not produce radical changes in the characteristics of the DAF molecule. However, when it is difficult to predict the exact effect of the substitution, deletion or insertion in advance of doing so, for example when modifying DAF receptor binding domain or an immune epitope, one skilled in the art will appreciate that the effect will be evaluated by routine screening assays. For example, a variant typically is made by site specific mutagenesis of the native DAF-encoding nucleic acid, expression of the variant nucleic acid in recombinant cell culture and, optionally, purification from the cell culture for example by immunoaffinity adsorption on a rabbit polyclonal anti-DAF column (in order to absorb the variant by at least one remaining immune epitope). The activity of the cell lysate or purified DAF variant is then screened in a suitable screening assay for the desired characteristic. For example, a change in the immunological character of the DAF, such as affinity for a given antibody, is measured by a competitive-type immunoassay. Changes in immunomodulator activity are measured by the C4b2a assay, although as more becomes known about the functions in vivo of sDAF and mDAF other assays will become useful in such screening. Modifications of such protein properties as redox or thermal stability, hydrophobicity, susceptibility to proteolytic degradation, or the tendency to aggregate with carriers or into multimers are assayed by methods well known to the artisan.

DAF from other species than humans, e.g. bovine, equine, ovine, porcine and the like is included within the scope hereof.

DAF preferably is made by synthesis in recombinant cell culture. In order to do so, it is first necessary to secure nucleic acid that encodes DAF. The inventors encountered considerable hardship in attempting to identify any nucleic acid encoding DAF. The sequence of the human mDNA encoding DAF that was ultimately determined is shown in FIG. 1. As noted above, study of cDNAs from hela cells led to the identification of cDNA encoding sDAF, shown in FIG. 2. Once this DNA has been identified it is a straight-forward matter for those skilled in the art to obtain it my nucleic acid hybridization to genomic libraries of human DNA or, if it is desired to obtain DNA encoding the DAF of another animal species, then by hybridization of DNA libraries from cells of that species. The hybridization analysis is now straight-forward because FIGS. 1 and 2 enable the preparation of very long synthetic probes that are perfect or nearly perfect matches for the target DNA.

It is possible that the cDNA or genomic library selected as the source for the DAF nucleic acid will not contain a single clone encoding the full length DAF, only partial clones. These partial clones and fragments are readily assembled into a full length DNA by cleaving the partial clones at selected restriction sites in overlapping sections, recovering each of the desired fragments and ligating them in the proper order and orientation. If necessary, oligonucleotides are prepared to supply any missing sequences.

The DAF-encoding nucleic acid is then ligated into a replicable vector for further cloning or for expression. Vectors are useful for performing two functions in collaboration with compatible host cells (a host-vector system). One function is to facilitate the cloning of the nucleic acid that encodes the DAF, i.e., to produce usable quantities of the nucleic acid. The other function is to direct the expression of DAF. One or both of these functions are performed by the vector-host system. The vectors will contain different components depending upon the function they are to perform as well as the host cell that is selected for cloning or expression.

Each vector will contain nucleic acid that encodes DAF as described above. Typically, this will be DNA that encodes the DAF in its mature form linked at its amino terminus to a secretion signal. This secretion signal preferably is the DAF preseuence that normally directs the secretion of DAF from human cells in vivo. However, suitable secretion signals also include signals from other animal DAFs, viral signals or signals from secreted polypeptides of the same or related species.

Expression and cloning vectors contain a nucleic acid sequence that enables the vector to replicate in one or more selected host cells. Generally, in cloning vectors this sequence is one that enables the vector to replicate independently of the host chromosomes, and includes origins of replication or autonomously replicating sequences. Such sequences are well-known for a variety of bacteria, yeast and viruses. The origin of replication from the well-known plasmid pBR322 is suitable for most gram negative bacteria, the 2μ plasmid origin for yeast and various viral origins (SV40, polyoma, adenovirus, VSV or BPV) are useful for cloning vectors in mammalian cells. Origins are not needed for mammalian expression vectors (the SV40 origin is used in the Examples only because it contains the early promoter). Most expression vectors are "shuttle vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA also is cloned by insertion into the host genome. This is readily accomplished with bacillus species, for example, by including in the vector a DNA sequence that is complementary to a sequence found in bacillus genomic DNA. Transfection of bacillus with this vector results in homologous recombination with the genome and insertion of DAF DNA. However, the recovery of genomic DNA encoding DAF is more complex than that of an exogenously replicated vector because restriction enzyme digestion is required to excise the DAF DNA.

Generally, DNA is inserted into a host genome for purposes of preparing a stable cell line or microbe for DAF expression.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

A suitable selection gene for use in yeast is the trp1 gene present in the yeast plasmid YRp7 (Stinchcomb et al., 1979, "Nature", 282; 39; Kingsman et al., 1979, "Gene", 7: 141; or Tschemper et al., 1980, "Gene", 10: 157). The trp1 gene provides a selection marker for a mutant strain of yeast lacking the ability to grow in tryptophan, for example ATCC No. 44076 or PEP41 (Jones, 1977, "Genetics", 85: 12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR) or thymidine kinase. Such markers enable the identification of cells which were competent to take up the DAF nucleic acid. The mammalian cell transformants.are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes DAF. Amplification is the process by which genes in greater demand for the production of a protein critical for growth are reiterated in tandem within the chromosomes of successive generations of recombinant cells. Increased quantities of DAF are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Nat'l. Acad. Sci. USA" 77: 4216. A particularly useful DHFR is a mutant DHFR that is highly resistant to MTX (EP 117,060A). This selection agent can be used with any otherwise suitable host, e.g. ATCC No. CCL61 CHO-K1), notwithstanding the presence of endogenous DHFR. The DHFR and DAF-encoding DNA then is amplified by exposure to an agent (methotrexate, or MTX) that inactivates the DHFR. One ensures that the cell requires more DHFR (and consequently amplifies all exogenous DNA) by selecting only for cells that can grown in successive rounds of ever-greater MTX concentration.

Other methods, vectors and host cells suitable for adaptation to the synthesis of the hybrid receptor in recombinant vertebrate cell culture are described in M. J. Gething et al., "Nature" 293: 620–625 (1981); N. Mantei et al., "Nature" 281: 40–46; and A. Levinson et al., EP 117,060A and 117,058A. A particularly useful starting plasmid for mammalian cell culture expression of DAF is pE342.HBV E400.D22 (also called pE348H-BVE400D22, EP 117,058A).

Expression vectors, unlike cloning vectors, should contain a promoter which is recognized by the host organism and is operably linked to the DAF nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. The presence or absence of a nutrient or a change in temperature. At this time a large number of promoters recognized by a variety of potential host cells are well known. These promoters are operably linked to DAF-encoding DNA by removing them from their gene of origin by restriction enzyme digestion, followed by insertion 5' to the start of codon for DAF. This is not to say that the genomic DAF promoter is not usable. However, heterologous promoters generally will result in greater transcription and higher yields of expressed DAF.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist then synthetic oligonucleotide adaptors or linkers are used in accord with conventional practice.

Promoters suitable for use with prokaryotic hosts include the β-lactamase and lactose promoter systems (Chang et al., 1978, "Nature", 275: 615; and Goeddel et al., 1979, "Nature", 281: 544), alkaline phosphatase, a tryptophan (trp) promoter system (Goeddel 1980, "Nucleic Acids Res." 8: 4057 and EPO Appln. Publ. No. 36,776) and hybrid promoters such as the tac promoter (H. de Boer et al., 1983, "Proc. Nat'l. Acad. Sci. USA" 80: 21-25). However, other known bacterial promoters are suitable. Their nucleotide sequences have been published, thereby enabling a skilled worker operably to ligate them to DNA encoding DAF (Siebenlist et al., 1980, "Cell" 20: 269) using linkers or adaptors to supply any required restriction sites. Promoters for use in bacterial systems also will contain a Shine-Dalgarno (S.D.) sequence operably linked to the DNA encoding DAF.

Suitable promoting sequences for use with yeast hosts include the promoters for 3-phosphoglycerate kinase (Hitzeman et al., 1980, "J. Biol. Chem.", 225: 2073) or other glycolytic enzymes (Hess et al., 1968, "J. Adv. Enzyme Reg.", 7: 149; and Holland, 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

DAF transcription from vectors kin mammalian host cells is controlled by promoter obtained from the genomes of viruses such as polyoma, cytomegalovirus, adenovirus, retroviruses, hepatitis-B virus and most preferably Simian Virus 40 (SV40), or from heterologous mammalian promoters, e.g. the actin promoter. The early and late promoters of the SV40 virus are conveniently obtained as an SV40 restriction fragment which also contains the SV40 viral origin of replication (Fiers et al., 1978, "Nature", 273: 113). Of course, promoters from the host cell or related species also are useful herein.

Transcription of DAF-encoding DNA by higher eukaryotes is increased by inserting an enhancer sequence into the vector. An enhancer is a nucleotide sequence, usually about from 10-300 bp, that acts on a promoter to increase its transcription and does so in a manner that is relatively orientation and position independent. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenoviral enhancers. The enhancer may be spliced into the vector at a position 5' or 3' to the DAF-encoding sequence, but is preferably located at a site 5' from the promoter.

Expression vectors used in eukaryotic host cells (yeast, fungi, insect, plant, animal, human or nucleated cells from other muticellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain regions that are transcribed as polyadenylated segments in the untranslated portion of the mRNA encoding DAF. the 3' untranslated regions also include transcription termination sites.

Suitable host cells for cloning or expressing the vectors herein are prokaryotes, yeast or higher eukaryotic cells. Prokaryotes include gram negative or gram positive organisms, for example E. coli or bacilli. A preferred cloning host is E. coli 294 (ATCC 31,446) although other gram negative or gram positive prokaryotes such as E. coli B, E. coli X1776 (ATCC 31,537), E. coli W3110 (ATCC 27,325), pseudomonas species, or Serratia Marcesans are suitable.

In addition to prokaryotes, eukaryotic microbes such as filamentous fungi or yeast are suitable hosts for DAF-encoding vectors. Saccharmoyces cerevisiae, or common baker's yeast, is the most commonly used among lower eukaryotic host microorganisms. However, a number of other genera, species and strains are commonly available and useful herein.

The preferred host cells for the expression of DAF are cells derived from multicellular organisms. DAF's large size, together with its intramolecular disulfide bond(s) and, in the case of mDAF, its unique post-translational processing, suggests that the host cell will optimally be of a higher phylogenetic order than the microbes if one is to expect the recombinant protein to demonstrate optimal conformational fidelity to native DAF. In addition, it may be desirable to glycosylate DAF. All of these functions can be best performed by higher eukaryotic cells. In principle, any higher eukaryotic cell culture is workable, whether from vertebrate or invertebrate culture, although cells from mammals such as humans are preferred. Propagation of such cells in culture is per se well known. See Tissue Culture, Academic Press, Kruse and Patterson, editors (1973). Examples of useful mammalian host cell lines are VERO and HeLa cells. Chinese hamster ovary cell lines, the WI38, BHK, COS-7, MDCK cell lines and human embryonic kidney cell line 293.

Host cells are transformed with the above-described expression or cloning vectors and cultured in conventional nutrient media modified as is appropriate for inducing promoters or selecting transformants containing amplified genes. The culture conditions, such as temperature, pH and the like, suitably are those previously used with the host cell selected for cloning or expression, as the case may be, and will be apparent to the ordinary artisan.

sDAF preferably is recovered from the culture medium as a secreted protein, although it also may be recovered from host cell lysates when directly expressed without a secretory signal. As a first step, the culture medium or lysate is centrifuged to remove particulate cell debris. DAF also is purified from contaminant soluble proteins for example by adsorption on a selection column e.g. ConA, elution, adsorption on an anti-sDAF or anti-mDAF immunoaffinity column and elution therefrom. Alternatively, other processes such as chromatography on alkyl Sepharose, silica or an anion or cation exchange resin or gel electrophoresis are used to separate the sDAF from contaminants. mDAF is recovered from transformant cell membranes using the method of Medof et al. (1984. Id.). mDAF variants in which the hydrophobic transmembrane region and/or the mDAF phosphatidylinositol-binding residue are deleted or substituted are recovered in the same fashion as sDAF, although variants in which the transmembrane region remains intact also are recovered from transformant cell membranes.

Since native DAF has a tendency to aggregate under some conditions it may be useful to stabilize the aggregative state of the multimers by providing in the separations a minor amount of a nonionic surfactant such as Tween or polyethylene glycol. A protease inhibitor such as PMSF also may be useful to inhibit proteolytic degradation during purification, and antibiotics may be included to prevent the growth of adventitious contaminants.

One skilled in the art will appreciate that purification methods suitable for native DAF may require modification to account for changes in the character of DAF or its variants upon expression in recombinant cell culture. For example, a DAF polypeptide produced in prokaryotic cell culture will not adsorb to Con-A Sepharose because it will be unglycosylated. In this case, other methods such as gel electrophoresis, ion exchange or immunoaffinity purification should be employed. Similarly, sDAF lipid-free C-terminal mDAF variants will not absorb as readily to hydrophobic adsorbents as does mDAF. Appropriate purification methods will be apparent to the artisan, depending upon the characteristics of the particular recombinant DAF.

DAF is prepared as a nontoxic salt with such ions as sodium, potassium, phosphate, chloride and the like. Generally, DAF is stored in phosphate buffered saline or may be lyophilized in the presence of an excipient including sugar alcohols, e.g. mannitol or sorbitol; monosaccharides, e.g., glucose, mannose, galactose or fructose; oligosaccharides such as maltose, lactose or sucrose; and proteins such as human serum albumin.

The foregoing excipients also may contribute to the stability of DAF to inactivation or precipitation upon aqueous storage, and may be used together with other stabilizers which are conventional per se. Such stabilizers include chelating agents, e.g. EDTA; antioxidants such as ascorbate or dithiothreitol; amino acids; and nonionic surfactants such as polyethylene glycol or block copolymers of polyethylene and polypropylene glycol.

DAF is administered to humans or animals in order to ameliorate various disorders stemming from immune dysfunction or misdirection, particularly defects in the humoral immune response. Examples include PNH, inflammatory conditions such as inflammatory bowel disease (colitis), rheumatoid arthritis, allograft rejection and the like. Treatment with DAF should be instituted early in the development of such disorders.

Therapeutic DAF compositions will contain a therapeutically effective dose of DAF in a pharmacologically acceptable carrier. The dose, carrier and route of administration selected will depend, among other factors, upon the disorder or condition to be treated, the condition of the patient, the desired route of administration, and the activity of the selected DAF variant. This is readily determined and monitored by the physician during the course of therapy.

The carrier for infusion or injection of DAF is a sterile isotonic aqueous solution, for example saline for injection or 5% dextrose. These preparations are injected or infused by intranasal, subcutaneous, intravenous, intraperitoneal or other conventional routes of administration. Preparations also are injected into the synonial fluid of arthritic joints.

DAF also is provided in a sustained release carrier. Suitable examples include semipermeable polymer matrices in the form of shaped articles, e.g. suppositories, or microcapsules. Implantable or microcapsules sustained relase matrices include polyactides (U.S. Pat. No. 3,773,919, EP58,481) copolymers of L-glutamic acid and gamma ethyl-L-glutamate (U. Sidman et al., 1983, "Biopolymers" 22(1): 547–556), poly (2-hydroxyethylmethacrylate) (R. Langer et al., 1981, "J. Biomed, Mater. Res." 15: 167–277 and R. Langer, 1982, "Chem Tech." 12: 98–105), ethylene vinyl acetate (R. Langer et al,, Id.), or poly-D-(—)-3-Hydroxybutyric acid (EP 133,988A). Sustained release DAF compositions also include liposomally entrapped DAF. Liposomes containng DAF are prepared by methods known per se: DE 3,218,121A; Epstein et al. 1985, "Proc. Natl. Acad. Sci. USA" 82: 3688-3602; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544,545; and EP 102,324A. Ordinarily the liposomes are of the small (about 200–800 Angstroms) unilamelar type in which the lipid content is greater than about 30 mol. % cholesterol, the selected proportion being adjusted for the optimal rate of DAF leakage.

Sustained release DAF preparations are implanted or injected into proximity to the site of inflammation or therapy, for example adjacent to arthritic joints or inflamed intestinal tissue.

Polyclonal rabbit or murine antisera raised against DAF is one described by Medof et al. (1984, Id.) Antisera are employed for immunoaffinity purification or DAF and in an ELISA assay for DAF. Antibody specific for the unique C-terminus of sDAF is made by immunizing an animal against an immunogenic sDAF conjugate, e.g. an immunogenic fusion made in recombinant cell culture as described elsewhere herein, and thereafter screening for the presence of anti-SDAF titer by passing the antiserum through a column of immobilized mDAF in order to adsorb antibodies directed against mDAF epitopes, incubating the unadsorbed antiserum in the presence of $^{125}$I-sDAF (prepared in substantially the same fashion as $^{125}$I-mDAF, Medof et al., 1984, Id.) to permit the unique sDAF epitopes to bind to the anti-DAF antibodies in the unadsorbed antiserum, and determining the amount of unbound $^{125}$I-sDAF, e.g. by adsorption on protein-A Sepharose.

The sDAF-specific antibodies in such antisera are prepared by adsorption as immobilized mDAF, recovery of the unadsorbed fraction, adsorption on immobilized SDAF and elution with pH 4–6 buffer to recover the SDAF-specific antibodies substantially free of MDAF antibodies. Alternatively, spleen cells from immunized animals showing anti-SDAF neutralizing titer are recovered and fused to myeloma cells or are transformed with EB virus in known fashion in order to prepare monoclonal sDAF-specific antibodies.

Neutralizing antibodies against DAF are useful when conjugated to immunogenic polypeptides as immunogens for raising anti-idiotypic antibodies having DAF activity. Such anti-idiotypic antibodies are useful for the same diagnostic and therapeutic purposes as DAF.

In order to simplify the Examples certain frequently occurring methods will be referenced by shorthand phrases.

"Plasmids" are designated by a low case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certian locations in the DNA. Such enzymes are called restriction enzymes, and the sites for which each is specific is called a restriction site. The various restriction enzymes used herein are commercially available and their reaction conditions, cofactors and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133—134).

"Filling" or "blunting" refers to the procedure by which the single stranded end in the cohesive terminus of a restriction enzyme-cleaved nucleic acid is converted to a double strand. This eliminates the cohesive terminus and forms a blunt end. This process is a versatile tool for converting a restriction cut end that may cohesive with the ends created by only one or a few other restriction enzymes into a terminus compatible with any blunt-cutting restriction endonuclease or other filled cohesive terminus. Typically, blunting is accomplished by incubating 2–15 μg of the target DNA in 10 mM MgCl$_2$, 1mM dithiothreitol, 50 mM NaCl, 10 mM Tris (pH 7.5) buffer at about 37° C. in the presence of 8 units of the Klenow fragment of DNA polymerase I and 250 μm of each of the four deoxynucleoside triphosphates. The incubation generally is terminated after 30 min. by phenol and chloroform extraction and ethanol precipitation.

"Recovery" or "isolation" of a given fragment of DNA from a restriction digest means separation of the digest on polyacrylamide or agrose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9:6103–6114, and D. Goeddel et al., 1980, "Nucleic Acids Res.: 8:4057.

"Northern" blotting is a method by which the presence of a cellular mRNA is confirmed by hybridization to a known, labelled oligonucleotide or DNA fragment. For the purposes herein, unless otherwise provided, Northern analysis shall mean electrophoretic separation of the mRNA on 1 percent agarose in the presence of a denaturant (formaldehyde −7%), transfer to nitrocellulose hybridization to the labelled fragment as described by T. Maniatis et al., Id., p. 202.

"Transformation" means introducing DNA into an organism so that the DNA is replicable, either as an extrachromosomal element or chromosomal integrate. Unless otherwise provided, the method used herein for transformation of *E. coli* is the CaCl$_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using know buffers and conditions with 10 units of T4 DNA ligase ("ligase") per 0.5 μg of approximately equimolar amounts of the DNA fragments to be ligated.

"Preparation" of DNA from transformants means isolating plasmid DNA from icrobial culture. Unless otherwise provided, the alkali/SDS method of Maniatis et al., Id., P. 90, may be used.

"Olignucleotides" are short length single or double stranded polydeoxynucleotides which are chemically synthesized by known methods and then purified on polyacrylamide gels.

The following examples are intended to merely illustrate the best mode now known for practicing the invention, but the invention is not to be considered limited thereto.

All literature citations herein are expressly incorporated by reference.

EXAMPLE 1

Identification of cDNA clones encoding DAF Cloning of human DAF

Human DAF was purified to homogeneity and 23 amino acids of N-terminal sequence were determined. Five of these were ambiguous.

A 69mer oligonucleotide probe based on this amino acid sequence was synthesized in vitro: The 32p-labelled (Kinased) probe and the following nucleotide sequence:

GCTGAGCACCTGCCCCCTGATGTGCCCAATGCCCAGCCTGCCCTGGAGGGCAAGAAACCCTTCC- (Seq. ID No. 7)

CTG

A Hela cell λcDNA library (approx. 1×10⁶ recombinants) was screened under low stringency conditions with this 69mer. Only one DAF clone (λ21) was identified, together with 6 false positives (by sequencing, these turned out to have limited nucleic acid homology with the probe, but a totally different amino and sequence). λ21 contained an insert encoding the sequence: Asp.Cys.Gly.Leu.Pro.Pro.Asp.Val.Pro.Asn.Ala.Gln.-Pro.Ala.Leu.Glu. Gly Arg.Thr. Ser.Phe.Pro.Gly., (Seq. ID No. 8) whereon the underlined residues differed from those identified by amino terminal sequencing.

The initial DAF clone (Clone λ21) was 1395 bp in length and contained a poly A tail but was missing the initiator methionine.

To determine the size of DAG MRNA a Northern bolt containing Hela cell Poly A+ RNA was screened 32p-labelled with DAF λ21. This probe hybridized to two messages of sizes approximately 1500bp and 2,000 bp. These were of roughly equal intensity.

To identify longer DAF clones with extensions at either of the 5' or 3' ends, we isolated 2 small restricton fragments from the 5' to 3' ends of ||21 as follows:

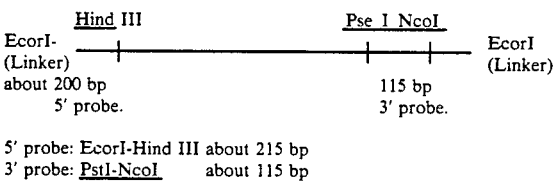

5' probe: EcorI-Hind III about 215 bp
3' probe: PstI-NcoI about 115 bp

These probes were labelled with ³²p and used to rescreen the Hela CDNA library for additional DAF - encoding clones. 2 more clones were identified, DAF λ41 and DAF λ47. These hybridized to both probes and were no longer than the DAF λ21 insert at approximately 2,000 bp and 2,200 bp respectively. Both of these clones contained aobut 780 bp of additional 3' untranslated sequence before the poly A tail. The 3'-untranslated sequence of the DAF gene contains a number of polyadenylation signals (AATAAA) and it appears that either an upstream of a downstream signal can be used to generate either the approx. 1,500 bp or the approx. 2,000 bp MRNAS.

At the 5'end, clone DAF λ41 was 55 bp longer than DAF λ21 and included an ATG for translation initiation. Clone DAF λ47 was 93 bp shorter than DAF λ21 at the 5'end.

Clone DAF 33 also was identified, but it only hybridized to the 5' probe. This clone was 71 bp longer than DAF λ21 at the 5' end, and therefore represented the longest extension in the 5' direction.

DAF λ21 and DAF λ41 were completely overlapping in the coding region of the protein and encoded a protein of 400 amino acids. DAF λ47 and DAF λ33 contained an apparent 'deletion' of 118 bp of coding region with respect to DAF λ21 and DAF λ41. On closer inspection it appeared that DAF λ21 and DAF λ41 contained an unspliced (unremoved) intron of 118 bp. Subsequently two more clones were identified, DAF λ35 and DAF λ37, one of which contains the same intron and one of which does not.

The frequency with which the unspliced form is present in the library (3 out of 6 clones) suggests that it is unlikely the unspliced clones represents improperly spliced message. Rather, there appear to be two forms of the DAF protein. These 2 forms are identical at amino acid positions 1-327, while having different C-terminal sequences. The unspliced form contains an additional 79 amino acids, the spliced form contains an additional 20 amino acids. Since the splice produces a change in reading frame there is no homology between the 2 proteins at the C-terminii.

From the hydropathy plots of the 2 DAF proteins, and from a comparision with the well-characterized Thy-1 membrane-bound glycoprotein, it is concluded that the spliced DAF CDNA directs synthesis of membrane-bound DAF, while the unspliced version encodes a soluble form.

EXAMPLE 2

Expression of DAF In Recombinant Cell Culture

Clones DAF λ33, λ41 and λ47 from Example 1 were each subcloned into pUC19, a readily available cloning vector for E. coli, by digesting each of the λ clones with EcoRI, recovering the DAF inserts from each, digesting pUC19 with EcoRI, ligating the inserts into opened pUC19 and transforming E. coli 294 with the each ligation mixture. pUC1933, pUC1941 and pUC1947 were recovered from ampicillin resistant colonies.

pUC1933, pUC1941 and pUC1947 were each digested with EcoRI and HindIII and the fragments (I, II and III respectively) containing the 5' end of the DAF gene, and the 3' ends of the sDAF and mDAF genes, respectively, were recovered. pUC19 digested with EcoRI was ligated to Fragments I and II in a three way ligation and pUC19sDAF was recovered from an ampicillin resistant E. coli colony. This was the subclone of the complete SDAF gene shown in FIGS. 2a-2c.

pUC19MDAF was constructed in the same way as pUC10sDAF except that Fragment III was used in place of Fragment II. This subclone contained the complete MDAF gene of FIG. 1a-1c.

PE348HVE400D122(also pE342 VE400D22, EP 117,058A) is digested wtih HindIII such that DHFR - containing fragment is recovered. The HindIII cohesive terminii are filled, the fragment digested with ClarI and the following fragment isolated

| | DHFR | HBsAg Poly A | pML | SV40 ori | |
|---|---|---|---|---|---|
| ClaI | | | | | HindIII (blunt) |

(Fragment a, 4084 bp)

PE348 MBV E400D22 also is digested with ClaI and SocII such that the 990 bp fragment containing the SV40 ori and HVsAg poly A sequence is recovered (Fragment b).

pUCsDAF and pUCmDAF were digested with EcoRI and each DAF encoding fragment isolated (Fragments CII and CIII, respectively).

Fragments CII, a and b are ligated in a three way ligation and transfected into *E. coli* 294. pE348sDAf is recovered from an ampicillin resistant colony. It contains the sDAF gene in proper orientation 3' to the SV40 early promoter. The SDAF gene is under the control of the SV40 early promoter in an expression vector suitable for transformation into and methotrexate selection and amplification in a mammalian host cell.

pE348mDAF is constructed in the same way except that Fragment CIII is used.

An alternative expression vector is constructed by digesting p342E (Crowley et al., 1983, "Mol. Cell. Biol." 3:44–55) with EcoRI and HpaI, and the vector fragment recovered. Either of pUC19mDAF or pUC19sDAF are digested with AccI (for MDAF) or blunt XhoII (for SDAF), filled, digested with EcorI and the DAF-encoding fragments recovered. The DAF fragments are ligated into the vector fragment and expression vectors recovered. This vector does not contain the DHFR gene, although cotransformation with pFD11 (Simonsen et al., 1983, "P.N.A.S.-USA" 80:2045-99) will produce satisfactory results.

PE348mDAF or pE348sDAF are co-transfected into DHFR⁻ CHO cells using conventional methods, inoculated into HAT medium and transformants selected by culture in media containing serial increases in methotrexate concentration to amplify the DHFR and DAF genes. A transformant clone is recovered that stably expresses DAF and secretes it into the culture medium. The sDAF is recovered from the medium by adsorption onto an immunoaffinity column containing protein-A sepharose immobilized rabbit polyclonal antibody to sDAF and elution with pH5 glycine buffer.

pE348mDAF is transformed into an amplified in DHFR⁻ CHO cells in the same way. mDAF is recovered by isolation from detergent lysates of host cell membranes in essentially the same fashion as mDAF has been recovered heretofore from red blood cell stroma.

EXAMPLE 3

Construction of Phospholipid Anchor Domain Fusion

In this Example a fusion protein was constructed in which the last 37 amino acids of membrane DAF predicted by the spliced cDNA were fused in-frame to the C-terminus of a truncated form of the Herpes Simplex Virus Type 1 (HSV 1) glycoprotein D (gD-1) that ordinarily is constitutively secreted to the culture medium since it lacks the C-terminal membrane-spanning domain (Lasky et al., "Bio/Technology 2:527 [1984]). A HindIII-HinfI fragment encoding the first 300 amino acids of HSV gD-1was ligated via a synthetic linker to XmnI-EcoRV fragment encoding the C-terminus of DAF (residues 316-347). The synthetic HinFI-XMnI linker (5'-ATTCGCCAAATAAAGCAAGTGG-AACC) encoded amino acid 301 of gD-1 and amino acids 311-317 of DAF and created an in-frame fusion.

The DNA encoding the gD-1/DAF fusion protein was inserted into a mammalian expression vector between an RSV promoter and an SV40 polyadenylation sequence by excision of the CAT gene and insertion of the fusion DNA (Gorman et al., "Proc. Natl. Acad. Sci. USA" 79:6777 [1982]) and transfected into CHO cells by the calcium-phosphate coprecipitation method (Wigler et al., "Proc. Natl. Acad. Sci. USA" 76:1373 [1979] and Simonsen et al., "Proc. Natl. Acad. Sci. USA" 80:2495 [1983]). Mouse dihydrofolate reductase cDNA provided a selectable marker for gene expression (Simonsen et al., "Proc. Natl. Acad. Sci. USA" 80:2495 [1983]). Stable cell lines derived from individual colonies were used for analysis. Cell lines expressing native gD-1or truncated Gd-1 were derived as described (Lasky et al., "Bio/Technology 2:527 [1984] and Berman et al., "Science" 222:525 [1983]). The resultant fusion protein (FIG. 3) contains the N-terminal 75% of gD-1 (residues 1–300) including the signal sequence and the C-terminal 10% (37amino acids) of membrane DAF including the 20 amino acid segment that is divergent between the two predicted DAF proteins and 17 amino acids of adjacent common sequence. The gD-1 /DAF fusion protein, native gD-1 (Berman et al., "Science" 222:524 [1983]), and the truncated gD-1 (Lasky et al., "Bio/Technology 2:527 [1984]) were expressed in CHO cells and localized by indirect immunofluorescence. Internal labeling of premeabilized cells expressing either native gD-1 or the gD-1 /DAF fusion showed similar localization of immunofluorescence in a perinuclear region, possibly the endoplasmic reticulum. Cells expresssing truncated gD-1showed intense fluorescence diffused throughout the cell cytoplasm. Immunofluorescence of intact (non-permeabilized) cells expressing full-length native Gd-1 shows that this protein is expressed on the cell surface as expected from its transmembrane domain. In contrast, no surface labeling was detected in cells expressing the truncated (secreted) form of gD-1. Cells expressing the gD-1/DAF fusion protein also show surface staining indicating that addition of the C-terminal domain of DAF redirects the secreted (truncated) gD-1to the plasma membrane.

The C-terminal segment of DAF encoded by the gD-1/DAF fusion contains a 17 amino acid hydrophobic resion at the C-terminus which may act as a transient membrane anchor thought to be removed post-translationally and replaced with PI-anchor (Low, M. G., "J. Biochem." 244:1–13 [1987]; Cross, G. A. M. "Cell" 48:179–181 [1987]; "Nature" 325:545 [1987]). The above experiments do not distinguish whether the fusion protein is anchored by a phospholipid anchor or by the 17 amino acid hydrophobic region. Therefore, to determine the nature of the attachment, CHO cells expressing either native gD-1 or gD/DAF fusion were incubated with purified phosphatidylinositol-specific phospholipase C (PI-PLC) from *Staphylococcus aureus* (Low, M. G., "Meth. Enzymol." 71:741 [1981]), and analyzed by indirect fluorescence and flow cytometry (FACS). Treatment with PI-PLC (which is free of proteolytic contaminants (Low et al, "Nature" 318:62 [1985]) resulted in a substantial reduction in the amount of gD-1/DAF on the cell surface as indicated by the marked decrease in relative cell fluorescence displayed on a log scale. Typically, 70–80% of the cell-surface gD-1/DAF was released by PI-PLC as indicaed by quantitative FACS analysis. In contrast, full-length native gD-1 expressed on the cell surface was unaffected by treatment with PI-PLC. The specificity of the release was further confirmed by the observation that the phospholipase C from either *Clostridium perfringens* or *Bacillus cereus*, which does not hydrolyze phosphotidylinositol (Little, C., "Meth. Enzymol." 71:725 [1981] and Takahashi, T. et al., "Meth Enzymol." 71:710 [1981]), did not release Gd-1/DAF from the plasma membrane.

The glycophospholipid anchor of DAF contains ethanolamine and glucosamine in addition to phosphatidylinositol (Medof et al., "Biochemistry" 25:6740 [1986]). The glycosylated phospholipid is thought to be linked to the protein through an amine bond between the terminal carboxyl group of the polypeptide and the amine group of ethanolamine (Low, M. G., "J. Biochem." 244:1-13 [1987] and Cross, G. A. M., "Cell" 48:179-181 [1987]). To confirm that the gD-1/DAF fusion protein is anchored by such a structure cells were metabolically labelled with either [³H]ethanolamine or [³⁵S]cysteine and the protein analyzed by immunopreocipitation. Multiple forms of gD-1/DAF, a 37 kD species and at least two larger, highly difuse species of approximately 46 kD and 52 kD, respectively, were detected by both polyclonal and monoclonal antibodies to HSV-1only in cells expressing gD-1/DAF. Preliminary pulse-chase experiments and experiments with neuraminidase suggest that the 37 kD species is a precursor, while the larger species represent mature, highly glycoslated forms of the protein. A [³H]Ethanolamine-labelled bands corresponding to the 46kD species is a precursor, while the larger species represent mature, highly glycosylated forms of the protein. [³H]Ethanolamine-labeled bands corresponding to 46 kD and 51 kD species but not a 37 kD species were specifically detected in cells expressing gD-1/DAF. Attachment of the clycophospholipid anchor is thought to be an early event in the biosynthesis of lipid-anchored proteins (Medof et al., "Biochemistry" 25:6740 [1986] and Berman et al. "Science" 222:524 [1983]). The absence of a [³H]ethanolamine-labeled band corresponding to the 37 kD gD-1/DAF precursor may be due to long pulse (16 h) used to label cells in this experiment. Native Gd-1 was not labeled with [³H]ethanolamine.

It was concluded that th Gd-1/DAF fusion protein is linked to the plasma membrane via phosphatidylinositol. This conclusion is supported by the following evidence. First, gD-1/DAF on the cell surface was sensitive to digestion with highly purified phosophatidylinositol-specific phospholipase C while native gD-1was unaffected. Second, broad specificity phospholipases were ineffective in releasing gD-1/DAF. Third, gD-1/DAF was specifically labeled by [³H]ethanolamine a component of the glyucophospholipid anchor. Thus, the information or "signal" necessary for directing the attachment of a phospholipid membrane anchor is contained within the C-terminal 37 amino acids of DAF. The concept that the C-terminal sequence plays a role in directing the attachment of lipid is supported by recent identification of multiple classes of the neural cell adhesion molecule (N-CAM) mRNa, presumably resulting from differential mRNA splicing. The different forms of N-CAM encoded by these mRNAs have different C-terminal domains, apparently resulting in membrane attachment either via a hydrophobic membrane-spanning domain, or via a phospholipid (Hemperly et al., "Proc. Natl. Acad. Sci. USA" 83:9822 [1986]). Inspection of the C-terminal amino acid sequences available for PI-anchored proteins has revealed no obvious homology, the only common feature being the presence of a short hydrophobic peptide (15-20 residues) at the C-terminus predicted by the cDNA sequence. This hydrophobic peptide, which could serve as a transient membrane anchor, is presumed to be removed during processing (Low, M. G. "J. Biochem." 244:1-13 [1987] and Cross, G. A. M., "Cell" 48:179-181 [1987]). The lack of sequence conservation in the C-terminal region of PI-anchored proteins suggests that the processing signal is conformational in character. Addition of a phospholipid membrane anchor by the means described above offers a novel mechanism for targeting soluble or secreted proteins to the cell surface membrane.

We claim:

1. Nucleic acid encoding a polypeptide comprising a decay accelerating factor phospholipid anchor recognition site fused to a polypeptide heterologous to said phospholipid anchor recognition site.

2. The nucleic acid of claim 1 which encodes, in 5' to 3' order, the heterologous polypeptide and the decay accelerating factor phospholipid anchor recognition site.

3. The nucleic acid of claim 1 wherein the phospholipid anchor recognition site contains about from 10 to 20 residues.

4. A recombinant host cell transformed with nucleic acid encoding a polypeptide comprising a decay accelerating factor phospholipid anchor recognition site fused to a polypeptide heterologous to said phospholipid anchor recognition site.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:1:

Thr Leu Leu Cys
1             4

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:2:

Lys Gln Lys Gln Lys
1               5

(2) INFORMATION FOR SEQ ID NO:3:

(i) SEQUENCE CHARACTERISTICS:
        (A) LENGTH: 4 amino acids
        (B) TYPE: amino acid
        (D) TOPOLOGY: linear (x i) SEQUENCE DESCRIPTION: SEQ ID NO:3:

Pro Leu Leu Ala
1           4

(2) INFORMATION FOR SEQ ID NO:4:

(i) SEQUENCE CHARACTERISTICS:
        (A) LENGTH: 4 amino acids
        (B) TYPE: amino acid
        (D) TOPOLOGY: linear (x i) SEQUENCE DESCRIPTION: SEQ ID NO:4:

Pro Asp Asp Glu
1           4

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: linear (x i) SEQUENCE DESCRIPTION: SEQ ID NO:5:

Thr Ser Ser Thr
1           4

(2) INFORMATION FOR SEQ ID NO:6:

(i) SEQUENCE CHARACTERISTICS:
        (A) LENGTH: 4 amino acids
        (B) TYPE: amino acid
        (D) TOPOLOGY: linear (x i) SEQUENCE DESCRIPTION: SEQ ID NO:6:

Gly Thr Thr Thr
1           4

(2) INFORMATION FOR SEQ ID NO:7:

(i) SEQUENCE CHARACTERISTICS:
        (A) LENGTH: 67 bases
        (B) TYPE: nucleic acid
        (C) STRANDEDNESS: single
        (D) TOPOLOGY: linear (x i) SEQUENCE DESCRIPTION: SEQ ID NO:7:

GCTGAGCACC TGCCCCCTGA TGTGCCCAAT GCCCAGCCTG CCCTGGAGGG 50

CAAGAAACCC TTCCCTG 67

(2) INFORMATION FOR SEQ ID NO:8:

(i) SEQUENCE CHARACTERISTICS:
        (A) LENGTH: 23 amino acids
        (B) TYPE: amino acid
        (D) TOPOLOGY: linear (x i) SEQUENCE DESCRIPTION: SEQ ID NO:8:

Asp Cys Gly Leu Pro Pro Asp Val Pro Asn Ala Gln Pro Ala Leu
1               5                   10                  15

```
Glu Gly Arg Thr Ser Phe Pro Gly
         20              23
```

( 2 ) INFORMATION FOR SEQ ID NO:9:

( i ) SEQUENCE CHARACTERISTICS:
        ( A ) LENGTH: 2116 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
CCGCTGGGCG TAGCTGCGAC TCGGCGGAGT CCCGGCGGCG CGTCCTTGTT  50

CTAACCCGGC GCGCC    ATG ACC GTC GCG CGG CCG AGC GTG      89
                    Met Thr Val Ala Arg Pro Ser Val
                     1                   5

CCC GCG GCG CTG CCC CTC CTC GGG GAG CTG CCC CGG CTG     128
Pro Ala Ala Leu Pro Leu Leu Gly Glu Leu Pro Arg Leu
         10              15                  20

CTG CTG CTG GTG CTG TTG TGC CTG CCG GCC GTG TGG GGT     167
Leu Leu Leu Val Leu Leu Cys Leu Pro Ala Val Trp Gly
                 25              30

GAC TGT GGC CTT CCC CCA GAT GTA CCT AAT GCC CAG CCA     206
Asp Cys Gly Leu Pro Pro Asp Val Pro Asn Ala Gln Pro
 35              40              45

GCT TTG GAA GGC CGT ACA AGT TTT CCC GAG GAT ACT GTA     245
Ala Leu Glu Gly Arg Thr Ser Phe Pro Glu Asp Thr Val
         50              55                  60

ATA ACG TAC AAA TGT GAA GAA AGC TTT GTG AAA ATT CCT     284
Ile Thr Tyr Lys Cys Glu Glu Ser Phe Val Lys Ile Pro
                 65              70

GGC GAG AAG GAC TCA GTG ATC TGC CTT AAG GGC AGT CAA     323
Gly Glu Lys Asp Ser Val Ile Cys Leu Lys Gly Ser Gln
 75              80              85

TGG TCA GAT ATT GAA GAG TTC TGC AAT CGT AGC TGC GAG     362
Trp Ser Asp Ile Glu Glu Phe Cys Asn Arg Ser Cys Glu
         90              95

GTG CCA ACA AGG CTA AAT TCT GCA TCC CTC AAA CAG CCT     401
Val Pro Thr Arg Leu Asn Ser Ala Ser Leu Lys Gln Pro
100              105             110

TAT ATC ACT CAG AAT TAT TTT CCA GTC GGT ACT GTT GTG     440
Tyr Ile Thr Gln Asn Tyr Phe Pro Val Gly Thr Val Val
        115              120                 125

GAA TAT GAG TGC CGT CCA GGT TAC AGA AGA GAA CCT TCT     479
Glu Tyr Glu Cys Arg Pro Gly Tyr Arg Arg Glu Pro Ser
                130              135

CTA TCA CCA AAA CTA ACT TGC CTT CAG AAT TTA AAA TGG     518
Leu Ser Pro Lys Leu Thr Cys Leu Gln Asn Leu Lys Trp
140              145             150

TCC ACA GCA GTC GAA TTT TGT AAA AAG AAA TCA TGC CCT     557
Ser Thr Ala Val Glu Phe Cys Lys Lys Lys Ser Cys Pro
        155              160

AAT CCG GGA GAA ATA CGA AAT GGT CAG ATT GAT GTA CCA     596
Asn Pro Gly Glu Ile Arg Asn Gly Gln Ile Asp Val Pro
165              170             175

GGT GGC ATA TTA TTT GGT GCA ACC ATC TCC TTC TCA TGT     635
Gly Gly Ile Leu Phe Gly Ala Thr Ile Ser Phe Ser Cys
        180              185                 190

AAC ACA GGG TAC AAA TTA TTT GGC TCG ACT TCT AGT TTT     674
Asn Thr Gly Tyr Lys Leu Phe Gly Ser Thr Ser Ser Phe
                195              200
```

-continued

```
TGT CTT ATT TCA GGC AGC TCT GTC CAG TGG AGT GAC CCG   713
Cys Leu Ile Ser Gly Ser Ser Val Gln Trp Ser Asp Pro
    205             210                 215

TTG CCA GAG TGC AGA GAA ATT TAT TGT CCA GCA CCA CCA   752
Leu Pro Glu Cys Arg Glu Ile Tyr Cys Pro Ala Pro Pro
            220                 225

CAA ATT GAC AAT GGA ATA ATT CAA GGG GAA CGT GAC CAT   791
Gln Ile Asp Asn Gly Ile Ile Gln Gly Glu Arg Asp His
230             235                 240

TAT GGA TAT AGA CAG TCT GTA ACG TAT GCA TGT AAT AAA   830
Tyr Gly Tyr Arg Gln Ser Val Thr Tyr Ala Cys Asn Lys
        245             250                 255

GGA TTC ACC ATG ATT GGA GAG CAC TCT ATT TAT TGT ACT   869
Gly Phe Thr Met Ile Gly Glu His Ser Ile Tyr Cys Thr
                260             265

GTG AAT AAT GAT GAA GGA GAG TGG AGT GGC CCA CCA CCT   908
Val Asn Asn Asp Glu Gly Glu Trp Ser Gly Pro Pro Pro
    270             275                 280

GAA TGC AGA GGA AAA TCT CTA ACT TCC AAG GTC CCA CCA   947
Glu Cys Arg Gly Lys Ser Leu Thr Ser Lys Val Pro Pro
            285                 290

ACA GTT CAG AAA CCT ACC ACA GTA AAT GTT CCA ACT ACA   986
Thr Val Gln Lys Pro Thr Thr Val Asn Val Pro Thr Thr
295             300                 305

GAA GTC TCA CCA ACT TCT CAG AAA ACC ACC ACA AAA ACC  1025
Glu Val Ser Pro Thr Ser Gln Lys Thr Thr Thr Lys Thr
        310             315                 320

ACC ACA CCA AAT GCT CAA GCA ACA CGG AGT ACA CCT GTT  1064
Thr Thr Pro Asn Ala Gln Ala Thr Arg Ser Thr Pro Val
                325             330

TCC AGG ACA ACC AAG CAT TTT CAT GAA ACA ACC CCA AAT  1103
Ser Arg Thr Thr Lys His Phe His Glu Thr Thr Pro Asn
    335             340                 345

AAA GGA AGT GGA ACC ACT TCA GGT ACT ACC CGT CTT CTA  1142
Lys Gly Ser Gly Thr Thr Ser Gly Thr Thr Arg Leu Leu
            350                 355

TCT GGG CAC ACG TGT TTC ACG TTG ACA GGT TTG CTT GGG  1181
Ser Gly His Thr Cys Phe Thr Leu Thr Gly Leu Leu Gly
360             365                 370

ACG CTA GTA ACC ATG GGC TTG CTG ACT TA GCCAAAGAAG    1220
Thr Leu Val Thr Met Gly Leu Leu Thr
        375             380 381
```

AGTTAAGAAG AAAATACACA CAAGTATACA GACTGTTCCT AGTTTCTTAG 1270

ACTTATCTGC ATATTGGATA AATAAATGC AATTGTGCTC TTCATTTAGG 1320

ATGCTTTCAT TGTCTTTAAG ATGTGTTAGG AATGTCAACA GAGCAAGGAG 1370

AAAAAAGGCA GTCCTGGAAT CACATTCTTA GCACACCTAC ACCTCTTGAA 1420

AATAGAACAA CTTGCAGAAT TGAGAGTGAT TCCTTTCCTA AAAGTGTAAG 1470

AAAGCATAGA GATTTGTTCG TATTTAGAAT GGGATCACGA GGAAAAGAGA 1520

AGGAAAGTGA TTTTTTTCCA CAAGATCTGT AATGTTATTT CCACTTATAA 1570

AGGAAATAAA AATGAAAACA TTATTTGGAT ATCAAAAGCA AATAAAACCC 1620

AATTCAGTCT CTTCTAAGCA AAATTGCTAA AGAGAGATGA ACCACATTAT 1670

AAAGTAATCT TTGGCTGTAA GGCATTTTCA TCTTTCCTTC GGGTTGGCAA 1720

AATATTTTAA AGGTAAAACA TGCTGGTGAA CCAGGGGTGT TGATGGTGAT 1770

AAGGGAGGAA TATAGAATGA AAGACTGAAT CTTCCTTTGT TGCACAAATA 1820

GAGTTTGGAA AAAGCCTGTG AAAGGTGTCT TCTTTGACTT AATGTCTTTA 1870

-continued

```
AAAGTATCCA GAGATACTAC AATATTAACA TAAGAAAAGA TTATATATTA   1920

TTTCTGAATC GAGATGTCCA TAGTCAAATT TGTAAATCTT ATTCTTTTGT   1970

AATATTTATT TATATTTATT TATGACAGTG AACATTCTGA TTTTACATGT   2020

AAAACAAGAA AAGTTGAAGA AGATATGTGA AGAAAATGT ATTTTCCTA     2070

AATAGAAATA AATGATCCCA TTTTTTGGTA AAAAAAAAA AAAAAA        2116
```

( 2 ) INFORMATION FOR SEQ ID NO:10:

( i ) SEQUENCE CHARACTERISTICS:
( A ) LENGTH: 2234 bases
( B ) TYPE: nucleic acid
( C ) STRANDEDNESS: single
( D ) TOPOLOGY: linear ( x i ) SEQUENCE DESCRIPTION: SEQ ID NO:10:

```
CCGCTGGGCG TAGCTGCGAC TCGGCGGAGT CCCGGCGGCG CGTCCTTGTT   50

CTAACCCGGC GCGCC    ATG ACC GTC GCG CG  CCG AGC GTG      89
                    Met Thr Val Ala Arg Pro Ser Val
                     1               5

CCC GCG GCG CTG CCC CTC CTC GGG GAG CTG CCC CGG CTG     128
Pro Ala Ala Leu Pro Leu Leu Gly Glu Leu Pro Arg Leu
        10              15              20

CTG CTG CTG GTG CTG TTG TGC CTG CCG GCC GTG TGG GGT     167
Leu Leu Leu Val Leu Leu Cys Leu Pro Ala Val Trp Gly
            25              30

GAC TGT GGC CTT CCC CCA GAT GTA CCT AAT GCC CAG CCA     206
Asp Cys Gly Leu Pro Pro Asp Val Pro Asn Ala Gln Pro
 35              40                      45

GCT TTG GAA GGC CGT ACA AGT TTT CCC GAG GAT ACT GTA     245
Ala Leu Glu Gly Arg Thr Ser Phe Pro Glu Asp Thr Val
         50              55                  60

ATA ACG TAC AAA TGT GAA GAA AGC TTT GTG AAA ATT CCT     284
Ile Thr Tyr Lys Cys Glu Glu Ser Phe Val Lys Ile Pro
                 65              70

GGC GAG AAG GAC TCA GTG ATC TGC CTT AAG GGC AGT CAA     323
Gly Glu Lys Asp Ser Val Ile Cys Leu Lys Gly Ser Gln
 75                      80                  85

TGG TCA GAT ATT GAA GAG TTC TGC AAT CGT AGC TGC GAG     362
Trp Ser Asp Ile Glu Glu Phe Cys Asn Arg Ser Cys Glu
             90                  95

GTG CCA ACA AGG CTA AAT TCT GCA TCC CTC AAA CAG CCT     401
Val Pro Thr Arg Leu Asn Ser Ala Ser Leu Lys Gln Pro
100                 105                 110

TAT ATC ACT CAG AAT TAT TTT CCA GTC GGT ACT GTT GTG     440
Tyr Ile Thr Gln Asn Tyr Phe Pro Val Gly Thr Val Val
            115                 120             125

GAA TAT GAG TGC CGT CCA GGT TAC AGA AGA GAA CCT TCT     479
Glu Tyr Glu Cys Arg Pro Gly Tyr Arg Arg Glu Pro Ser
                130                 135

CTA TCA CCA AAA CTA ACT TGC CTT CAG AAT TTA AAA TGG     518
Leu Ser Pro Lys Leu Thr Cys Leu Gln Asn Leu Lys Trp
140                 145                 150

TCC ACA GCA GTC GAA TTT TGT AAA AAG AAA TCA TGC CCT     557
Ser Thr Ala Val Glu Phe Cys Lys Lys Lys Ser Cys Pro
            155                 160

AAT CCG GGA GAA ATA CGA AAT GGT CAG ATT GAT GTA CCA     596
Asn Pro Gly Glu Ile Arg Asn Gly Gln Ile Asp Val Pro
165                 170                 175

GGT GGC ATA TTA TTT GGT GCA ACC ATC TCC TTC TCA TGT     635
Gly Gly Ile Leu Phe Gly Ala Thr Ile Ser Phe Ser Cys
```

```
                  180                         185                              190
AAC  ACA  GGG  TAC  AAA  TTA  TTT  GGC  TCG  ACT  TCT  AGT  TTT   674
Asn  Thr  Gly  Tyr  Lys  Leu  Phe  Gly  Ser  Thr  Ser  Ser  Phe
               195                      200

TGT  CTT  ATT  TCA  GGC  AGC  TCT  GTC  CAG  TGG  AGT  GAC  CCG   713
Cys  Leu  Ile  Ser  Gly  Ser  Ser  Val  Gln  Trp  Ser  Asp  Pro
     205                      210                      215

TTG  CCA  GAG  TGC  AGA  GAA  ATT  TAT  TGT  CCA  GCA  CCA  CCA   752
Leu  Pro  Glu  Cys  Arg  Glu  Ile  Tyr  Cys  Pro  Ala  Pro  Pro
               220                      225

CAA  ATT  GAC  AAT  GGA  ATA  ATT  CAA  GGG  GAA  CGT  GAC  CAT   791
Gln  Ile  Asp  Asn  Gly  Ile  Ile  Gln  Gly  Glu  Arg  Asp  His
230                      235                      240

TAT  GGA  TAT  AGA  CAG  TCT  GTA  ACG  TAT  GCA  TGT  AAT  AAA   830
Tyr  Gly  Tyr  Arg  Gln  Ser  Val  Thr  Tyr  Ala  Cys  Asn  Lys
               245                      250                      255

GGA  TTC  ACC  ATG  ATT  GGA  GAG  CAC  TCT  ATT  TAT  TGT  ACT   869
Gly  Phe  Thr  Met  Ile  Gly  Glu  His  Ser  Ile  Tyr  Cys  Thr
                    260                      265

GTG  AAT  AAT  GAT  GAA  GGA  GAG  TGG  AGT  GGC  CCA  CCA  CCT   908
Val  Asn  Asn  Asp  Glu  Gly  Glu  Trp  Ser  Gly  Pro  Pro  Pro
     270                      275                      280

GAA  TGC  AGA  GGA  AAA  TCT  CTA  ACT  TCC  AAG  GTC  CCA  CCA   947
Glu  Cys  Arg  Gly  Lys  Ser  Leu  Thr  Ser  Lys  Val  Pro  Pro
               285                      290

ACA  GTT  CAG  AAA  CCT  ACC  ACA  GTA  AAT  GTT  CCA  ACT  ACA   986
Thr  Val  Gln  Lys  Pro  Thr  Thr  Val  Asn  Val  Pro  Thr  Thr
295                      300                      305

GAA  GTC  TCA  CCA  ACT  TCT  CAG  AAA  ACC  ACC  ACA  AAA  ACC   1025
Glu  Val  Ser  Pro  Thr  Ser  Gln  Lys  Thr  Thr  Thr  Lys  Thr
               310                      315                      320

ACC  ACA  CCA  AAT  GCT  CAA  GCA  ACA  CGG  AGT  ACA  CCT  GTT   1064
Thr  Thr  Pro  Asn  Ala  Gln  Ala  Thr  Arg  Ser  Thr  Pro  Val
                    325                      330

TCC  AGG  ACA  ACC  AAG  CAT  TTT  CAT  GAA  ACA  ACC  CCA  AAT   1103
Ser  Arg  Thr  Thr  Lys  His  Phe  His  Glu  Thr  Thr  Pro  Asn
     335                      340                      345

AAA  GGA  AGT  GGA  ACC  ACT  TCA  GGT  ACT  ACC  CGT  CTT  CTA   1142
Lys  Gly  Ser  Gly  Thr  Thr  Ser  Gly  Thr  Thr  Arg  Leu  Leu
               350                      355

TCT  GGT  TCT  CGT  CCT  GTC  ACC  CAG  GCT  GGT  ATG  CGG  TGG   1181
Ser  Gly  Ser  Arg  Pro  Val  Thr  Gln  Ala  Gly  Met  Arg  Trp
360                      365                      370

TGT  GAT  CGT  AGC  TCA  CTG  CAG  TCT  CGA  ACT  CCT  GGG  TTC   1220
Cys  Asp  Arg  Ser  Ser  Leu  Gln  Ser  Arg  Thr  Pro  Gly  Phe
               375                      380                      385

AAG  CGA  TCC  TTC  CAC  TTC  AGC  CTC  CCA  AGT  AGC  TGG  TAC   1259
Lys  Arg  Ser  Phe  His  Phe  Ser  Leu  Pro  Ser  Ser  Trp  Tyr
                    390                      395

TAC  AGG  GCA  CAC  GTG  TTT  CAC  GTT  GAC  AGG  TTT  GCT  TGG   1298
Tyr  Arg  Ala  His  Val  Phe  His  Val  Asp  Arg  Phe  Ala  Trp
     400                      405                      410

GAC  GCT  AGT  AAC  CAT  GGG  CTT  GCT  GAC  TTA  GCC  AAA  GAA   1337
Asp  Ala  Ser  Asn  His  Gly  Leu  Ala  Asp  Leu  Ala  Lys  Glu
               415                      420

GAG  TTA  AGA  AGA  AAA  TAC  ACA  CAA  GTA  TAC  AGA  CTG  TTC   1376
Glu  Leu  Arg  Arg  Lys  Tyr  Thr  Gln  Val  Tyr  Arg  Leu  Phe
425                      430                      435

CTA  GTT  TCT  TAGAC TTATCTGCAT ATTGGATAAA ATAAATGCAA              1420
Leu  Val  Ser
          440
```

```
TTGTGCTCTT  CATTTAGGAT  GCTTTCATTG  TCTTTAAGAT  GTGTTAGGAA  1470
TGTCAACAGA  GCAAGGAGAA  AAAAGGCAGT  CCTGGAATCA  CATTCTTAGC  1520
ACACCTACAC  CTCTTGAAAA  TAGAACAACT  TGCAGAATTG  AGAGTGATTC  1570
CTTTCCTAAA  AGTGTAAGAA  AGCATAGAGA  TTTGTTCGTA  TTTAGAATGG  1620
GATCACGAGG  AAAAGAGAAG  GAAAGTGATT  TTTTTCCACA  AGATCTGTAA  1670
TGTTATTTCC  ACTTATAAAG  GAAATAAAAA  TGAAAACATT  ATTTGGATAT  1720
CAAAAGCAAA  TAAAACCCAA  TTCAGTCTCT  TCTAAGCAAA  ATTGCTAAAG  1770
AGAGATGAAC  CACATTATAA  AGTAATCTTT  GGCTGTAAGG  CATTTCATC   1820
TTTCCTTCGG  GTTGGCAAAA  TATTTAAAG   GTAAACATG   CTGGTGAACC  1870
AGGGGTGTTG  ATGGTGATAA  GGGAGGAATA  TAGAATGAAA  GACTGAATCT  1920
TCCTTTGTTG  CACAAATAGA  GTTTGGAAAA  AGCCTGTGAA  AGGTGTCTTC  1970
TTTGACTTAA  TGTCTTTAAA  AGTATCCAGA  GATACTACAA  TATTAACATA  2020
AGAAAAGATT  ATATATTATT  TCTGAATCGA  GATGTCCATA  GTCAAATTTG  2070
TAAATCTTAT  TCTTTTGTAA  TATTTATTTA  TATTTATTTA  TGACAGTGAA  2120
CATTCTGATT  TTACATGTAA  AACAAGAAAA  GTTGAAGAAG  ATATGTGAAG  2170
AAAAATGTAT  TTTTCCTAAA  TAGAAATAAA  TGATCCCATT  TTTTGGTAAA  2220
AAAAAAAAAA  AAAA  2234
```